US012611313B2

(12) United States Patent
Bowden et al.

(10) Patent No.: US 12,611,313 B2
(45) Date of Patent: Apr. 28, 2026

(54) MINIMALLY INVASIVE COMPLIANT DEVICES FOR TOTAL LUMBAR DISC REPLACEMENT

(71) Applicant: 33 Medical, Inc., Boca Raton, FL (US)

(72) Inventors: Anton Edis Bowden, Lindon, UT (US); Daniel James Orr, Spanish Fork, UT (US)

(73) Assignee: 33 MEDICAL, INC., Boca Raton, FL (US)

( * ) Notice: Subject to any disclaimer, the term of this patent is extended or adjusted under 35 U.S.C. 154(b) by 0 days.

(21) Appl. No.: 18/629,688

(22) Filed: Apr. 8, 2024

(65) Prior Publication Data

US 2024/0335296 A1     Oct. 10, 2024

Related U.S. Application Data

(60) Provisional application No. 63/457,482, filed on Apr. 6, 2023.

(51) Int. Cl.
*A61F 2/44*       (2006.01)
*A61F 2/30*       (2006.01)

(52) U.S. Cl.
CPC .. *A61F 2/4425* (2013.01); *A61F 2002/30016* (2013.01); *A61F 2002/30112* (2013.01);
(Continued)

(58) Field of Classification Search
CPC ... A61F 2/442; A61F 2/4425; A61F 2002/443
See application file for complete search history.

(56) References Cited

U.S. PATENT DOCUMENTS

| 2,474,911 A | 7/1949 | Pierce et al. |
| 4,502,161 A | 3/1985 | Wall |

(Continued)

FOREIGN PATENT DOCUMENTS

| CA | 2703807 A1 | 11/2011 |
| CN | 101426451 B | 6/2011 |

(Continued)

OTHER PUBLICATIONS

Allemann et al., "Hyaluronic acid gel (Juvéderm™) preparations in the treatment of facial wrinkles and folds" Clinical Interventions in Aging, vol. 3, No. 4, 2008, pp. 629-634.

(Continued)

*Primary Examiner* — Ellen C Hammond
(74) *Attorney, Agent, or Firm* — Husch Blackwell LLP; Andrew C. Landsman

(57)     ABSTRACT

Minimally invasive compliant devices for spinal disc replacement are discussed herein. In various embodiments, the device comprises a contact-aided compliant mechanism comprising a first rigid component, a second rigid component, a third rigid component, a first flexible component, a second flexible component. Additionally, the first flexible component can be disposed between the first rigid component and the second rigid component while the second flexible components disposed between the second rigid component and the third rigid component. In many embodiments, the rigid components can include a bearing surface, wherein the bearing surface selectively engages another bearing surface of another rigid component.

20 Claims, 27 Drawing Sheets

(52) U.S. Cl.
CPC .............. *A61F 2002/30176* (2013.01); *A61F 2002/30291* (2013.01); *A61F 2002/30878* (2013.01); *A61F 2002/30985* (2013.01); *A61F 2002/443* (2013.01)

(56) References Cited

U.S. PATENT DOCUMENTS

| | | | |
|---|---|---|---|
| 4,526,909 A | 7/1985 | Urist | |
| 4,580,440 A | 4/1986 | Reid et al. | |
| 4,837,285 A | 6/1989 | Berg et al. | |
| 5,024,659 A | 6/1991 | Sjostrom | |
| 5,134,122 A | 7/1992 | Orsolini | |
| 5,171,279 A | 12/1992 | Mathews | |
| 5,286,763 A | 2/1994 | Gerhart et al. | |
| 5,290,271 A | 3/1994 | Jernberg | |
| 5,344,452 A | 9/1994 | Lemperle | |
| 5,352,715 A | 10/1994 | Wallace et al. | |
| 5,480,440 A | 1/1996 | Kambin | |
| 5,571,182 A | 11/1996 | Ersek et al. | |
| 5,599,852 A | 2/1997 | Scopelianos et al. | |
| 5,641,514 A | 6/1997 | Cho | |
| 5,989,291 A * | 11/1999 | Ralph | A61F 2/4425 |
| | | | 623/17.15 |
| 6,107,466 A | 8/2000 | Hasan et al. | |
| 6,121,341 A | 9/2000 | Sawhney et al. | |
| 6,129,761 A | 10/2000 | Hubbell | |
| 6,160,033 A | 12/2000 | Nies | |
| 6,183,518 B1 | 2/2001 | Ross et al. | |
| 6,264,650 B1 | 7/2001 | Hovda et al. | |
| 6,264,659 B1 | 7/2001 | Ross et al. | |
| 6,264,695 B1 | 7/2001 | Stoy | |
| 6,284,872 B1 | 9/2001 | Celeste et al. | |
| 6,309,420 B1 | 10/2001 | Preissman | |
| 6,335,028 B1 | 1/2002 | Vogel et al. | |
| 6,355,705 B1 | 3/2002 | Bond et al. | |
| 6,383,200 B1 | 5/2002 | Wotton | |
| 6,391,059 B1 | 5/2002 | Lemperle et al. | |
| 6,432,437 B1 | 8/2002 | Hubbard | |
| 6,468,274 B1 | 10/2002 | Alleyne et al. | |
| 6,468,310 B1 * | 10/2002 | Ralph | A61F 2/4425 |
| | | | 623/17.13 |
| 6,500,180 B1 | 12/2002 | Foley et al. | |
| 6,579,290 B1 | 6/2003 | Hardcastle et al. | |
| 6,602,248 B1 | 8/2003 | Sharps et al. | |
| 6,652,883 B2 | 11/2003 | Goupil et al. | |
| 6,673,113 B2 * | 1/2004 | Ralph | A61F 2/442 |
| | | | 606/907 |
| 6,713,527 B2 | 3/2004 | Bond et al. | |
| 6,730,091 B1 | 5/2004 | Pfefferle et al. | |
| 6,887,272 B2 | 5/2005 | Shinomiya et al. | |
| 7,060,103 B2 | 6/2006 | Carr et al. | |
| 7,131,997 B2 | 11/2006 | Bourne et al. | |
| 7,153,325 B2 * | 12/2006 | Kim | A61F 2/4425 |
| | | | 623/17.15 |
| 7,306,627 B2 | 12/2007 | Tanagho et al. | |
| 7,341,601 B2 | 3/2008 | Eisermann et al. | |
| 7,442,389 B2 | 10/2008 | Quelle et al. | |
| 7,537,612 B2 * | 5/2009 | Kunzler | A61F 2/4425 |
| | | | 623/17.13 |
| RE41,286 E | 4/2010 | Atkinson et al. | |
| 8,127,770 B2 | 3/2012 | Alleyne et al. | |
| 8,357,795 B2 | 1/2013 | Lebreton | |
| 8,506,633 B2 | 8/2013 | Trieu | |
| 8,586,089 B2 | 11/2013 | Anderson | |
| 9,351,769 B2 | 5/2016 | Alleyne et al. | |
| 12,156,956 B2 | 12/2024 | Young et al. | |
| 2002/0045942 A1 | 4/2002 | Ham | |
| 2002/0120259 A1 | 8/2002 | Lettice et al. | |
| 2002/0176893 A1 | 11/2002 | Wironen et al. | |
| 2003/0009223 A1 | 1/2003 | Fehling et al. | |
| 2003/0009235 A1 | 1/2003 | Manrique et al. | |
| 2003/0014051 A1 | 1/2003 | Woloszko | |
| 2003/0014112 A1 | 1/2003 | Ralph et al. | |
| 2003/0040742 A1 | 2/2003 | Underwood et al. | |
| 2003/0149490 A1 | 8/2003 | Ashman | |

| | | | |
|---|---|---|---|
| 2003/0158545 A1 | 8/2003 | Hovda et al. | |
| 2003/0211083 A1 | 11/2003 | Vogel et al. | |
| 2003/0212395 A1 | 11/2003 | Woloszko et al. | |
| 2003/0236573 A1 | 12/2003 | Evans et al. | |
| 2004/0024465 A1 | 2/2004 | Lambrecht et al. | |
| 2004/0054414 A1 | 3/2004 | Trieu et al. | |
| 2004/0078077 A1 | 4/2004 | Binette et al. | |
| 2004/0091540 A1 | 5/2004 | Desrosiers et al. | |
| 2004/0115240 A1 | 6/2004 | Narhi et al. | |
| 2004/0127963 A1 | 7/2004 | Uchida et al. | |
| 2004/0172019 A1 | 9/2004 | Ferree | |
| 2004/0210226 A1 | 10/2004 | Trieu | |
| 2005/0031666 A1 | 2/2005 | Trieu | |
| 2005/0038515 A1 * | 2/2005 | Kunzler | A61F 2/4425 |
| | | | 623/17.13 |
| 2005/0100510 A1 | 5/2005 | Falco | |
| 2005/0187628 A1 | 8/2005 | Michelson | |
| 2006/0002971 A1 | 1/2006 | Saltzman et al. | |
| 2006/0052795 A1 | 3/2006 | White | |
| 2006/0089714 A1 * | 4/2006 | Liu | A61F 2/4425 |
| | | | 623/17.11 |
| 2006/0206116 A1 | 9/2006 | Yeung | |
| 2006/0229621 A1 | 10/2006 | Cadmus | |
| 2006/0252297 A1 | 11/2006 | Culpepper | |
| 2006/0263830 A1 | 11/2006 | Grinstaff et al. | |
| 2007/0093904 A1 * | 4/2007 | Biedermann | A61F 2/44 |
| | | | 623/17.13 |
| 2007/0093907 A1 | 4/2007 | Goupil et al. | |
| 2007/0162019 A1 | 7/2007 | Burns et al. | |
| 2007/0168038 A1 | 7/2007 | Trieu | |
| 2007/0173936 A1 | 7/2007 | Hester et al. | |
| 2008/0096976 A1 | 4/2008 | Alleyne et al. | |
| 2008/0107744 A1 | 5/2008 | Chu | |
| 2008/0124371 A1 | 5/2008 | Turos et al. | |
| 2008/0160060 A1 | 7/2008 | Ellies | |
| 2008/0166386 A1 | 7/2008 | Caseres et al. | |
| 2008/0299172 A1 | 12/2008 | Young et al. | |
| 2009/0024218 A1 | 1/2009 | Frigg et al. | |
| 2009/0074728 A1 | 3/2009 | Gronthos et al. | |
| 2009/0076618 A1 | 3/2009 | Auberger | |
| 2009/0118836 A1 | 5/2009 | Cordaro | |
| 2009/0318976 A1 | 12/2009 | Gabriel et al. | |
| 2010/0004699 A1 | 1/2010 | Alleyne et al. | |
| 2010/0004700 A1 | 1/2010 | Alleyne | |
| 2010/0010549 A1 | 1/2010 | Alleyne et al. | |
| 2010/0041788 A1 | 2/2010 | Voigts et al. | |
| 2010/0316715 A1 | 12/2010 | Andersson | |
| 2011/0230919 A1 | 9/2011 | Alleyne | |
| 2012/0078313 A1 * | 3/2012 | Hasse | A61F 2/442 |
| | | | 606/53 |
| 2012/0310140 A1 | 12/2012 | Kramer et al. | |
| 2020/0188660 A1 | 6/2020 | Franke et al. | |
| 2020/0289285 A1 * | 9/2020 | Siemionow | A61B 17/7064 |
| 2020/0340520 A1 | 10/2020 | Bullard | |
| 2020/0345896 A1 | 11/2020 | Peyman | |
| 2021/0025443 A1 | 1/2021 | Lazzaro | |
| 2021/0369371 A1 | 12/2021 | Dearden et al. | |
| 2022/0047397 A1 | 2/2022 | Howell et al. | |
| 2022/0168114 A1 * | 6/2022 | Berry | A61F 2/30771 |
| 2022/0218878 A1 | 7/2022 | Rai et al. | |
| 2024/0337286 A1 * | 10/2024 | Bowden | F16C 11/12 |

FOREIGN PATENT DOCUMENTS

| | | | |
|---|---|---|---|
| CN | 101502676 B | 2/2013 | |
| CN | 110439922 A | 11/2019 | |
| DE | 102014006727 B3 | 10/2015 | |
| FR | 2446952 A1 | 8/1980 | |
| JP | 2008509935 A | 4/2008 | |
| JP | 6508795 B1 | 5/2019 | |
| KR | 20090043973 A | 5/2009 | |
| WO | 9210982 A1 | 7/1992 | |
| WO | 9840113 A1 | 9/1998 | |
| WO | 0044394 A1 | 8/2000 | |
| WO | 0044808 A1 | 8/2000 | |
| WO | 0168721 A1 | 9/2001 | |
| WO | 03049669 A2 | 6/2003 | |
| WO | 2005046746 A2 | 5/2005 | |

(56) References Cited

FOREIGN PATENT DOCUMENTS

| | | |
|---|---|---|
| WO | 2008005676 A2 | 1/2008 |
| WO | 2009155656 A1 | 12/2009 |
| WO | 2013006671 A2 | 1/2013 |

OTHER PUBLICATIONS

Artecoll Product History. Downloaded from <www.artecoll.com> on Jun. 2, 2010, pp. 1-2.

Baumann et al., "An injectable drug delivery platform for sustained combination therapy," Journal of Controlled Release, vol. 138, No. 3, 2009, pp. 205-213.

Bayston, et al. "The sustained release of antimicrobial drugs from bone cement. An appraisal of laboratory investigations and their significance," J. Bone Joint Surg. (Br), vol. 62, No. 4, 1982, pp. 460-464.

Bergeret-Galley et al., "The Value of a New Filler Material in Corrective and Cosmetic Surgery: Dermalive and DermaDeep", Aesthetic Plastic Surgery, vol. 25, 2001, pp. 249-255.

Carruthers "Artecoll - An injectable micro-implant for longlasting soft tissue augmentation," Skin Therapy Letter, vol. 4, No. 2, Jan. 1999, pp. 1-6.

Cohen et al., "Artecoll: A Long-Lasting Injectable Wrinkle Filler Material: Report of a Controlled, Randomized, Multicenter Clinical Trial of 251 Subjects", Plastic Reconst. Surg., vol. 114, No. 4, Sep. 15, 2004, pp. 964-976.

Comparison chart [online], Retrieved from https://tru-flo.com/wp-content/uploads/2020/09/Tru-Flo-Viscosity-Comparison-Chart.pdf, 2018,1 page.

Extended European Search Report received for European Patent Application No. 16738015.3, mailed on Apr. 20, 2017, 9 pages.

Faught, et al., "The Effects of Laser Energy on the Arterial Wall", Annals of Vascular Surgery, vol. 4, No. 2, 1990, pp. 198-207.

FDA Approval Document for juvederm™, Device generic name: Injectable Dermal Filler, Retrieved from https://www.accessdata.fda.gov/cdrh_docs/pdf5/p050047b.pdf, 2006, 19 pages.

Goisis, M., Injections in Aesthetic Medicine: Atlas of Full-face and Full-body Treatment; Springer Science & Business Media, 2013, pp. 279-280.

Hoffman, Klaus, "Volumizing effects of a smooth, highly cohesive, viscous 20-mg/mL hyaluronic acid volumizing filler: prospective European study," BMC Dermatology vol. 9, 2009, pp. 1-9.

Hu et al., "Preparation of uniform poly(methyl methacrylate) particles by dispersion polymerization", Acta Polymerica Sinica, 2003, pp. 540-545.

International Preliminary Report on Patentability received for PCT Application No. PCT/US2024/023616, mailed on Oct. 16, 2025, 6 pages.

International Preliminary Report on Patentability for International Application No. PCT/US2005/031225 dated Mar. 8, 2007, 8 pages.

International Preliminary Report on Patentability received for PCT Application No. PCT/US2005/030678 dated Mar. 8, 2007, 8 pages.

International Search Report & Written Opinion received for International Pat. Appl. No. PCT/US2024/032275, mailed on Oct. 17, 2024, 15 pages.

International Search Report and Written Opinion received for PCT Application No. PCT/US2024/023606, mailed on Jul. 17, 2024, 7 pages.

International Search Report and Written Opinion received for PCT Application No. PCT/US2024/023616, mailed on Aug. 27, 2024, 9 pages.

International Search Report and Written Opinion received for PCT Patent Application No. PCT/US2016/013718, mailed on Jun. 22, 2016, 14 pages.

Kablik et al., "Comparative physical properties of hyaluronic acid dermal fillers", Dermatol Surg, vol. 35, 2009, pp. 302-312.

Kim et al., "Effect of Crosslinking Agents on the Morphology of Polymer Particles Produced by One-Step Seeded Polymerization", Macromolecular Research, vol. 17, No. 4, 2009, pp. 250-258.

Lautenschlager, Hans, "Hyaluronic Acid—A Legendary Agent" Kosmetische Praxis, vol. 4 , 2008, pp. 1-3.

Lemperle et al. "ArteFill Permanent Injectable for Soft Tissue Augmentation: I. Mechanism of Action and Injection Techniques," Aesth Plast Surg, vol. 34, 2010, pp. 264-272.

Liga et al. "Safe and cost-effective rapid-prototyping of multilayer PMMA microfluidic devices," Microfluid Nanofluid, vol. 20, No. 164, 2016, pp. 1-12.

Masala et al., "Percutaneous Vertebroplasty in Painful Schmorl Nodes," Cardiovasc Intervent Radiol, vol. 29, Published Online Nov. 18, 2005, pp. 97-101.

Omlor, et al., "Injection of a polymerized hyaluronic acid/collagen hydrogel matrix in an in vivo porcine disc degeneration model", European Spine Journal, vol. 21, 2012, pp. 1700-1708.

Rodrigues et al., "Two-solution bone cements with cross-linked micro and nano-particles for vertebral fracture applications: Effects of zirconium dioxide content on the material and setting properties", J Biomed Mater Res Part B: Appl Biomater 92B, 2010, pp. 13-23.

Sundaram et al., "Comparision of the Rheological Properties of Viscosity and Elasticity in Two Categories of Soft Tissue Fillers: Calcium Hydroxylapatite and Hyaluronic Acid", Dermatol Surg, vol. 36, 2010, pp. 1859-1865.

Wahlig et al., "Pharmacokinetic study of gentamicin-loaded cement in total hip replacements. Comparative effects of varying dosage." J Bone Joint Surg. (Br), vol. 66-B, No. 2, Mar. 1994, pp. 175-179. 2018, 1 page.

Wang et al., "Combination of Hyaluronic Acid Hydrogel Scaffold and PLGA Microspheres for Supporting Survival of Neural Stem Cells," Pharmaceutical Research, vol. 28, May 4, 2011, pp. 1406-1414.

* cited by examiner

100

100

102

104

100

102

104

200

500

504

502

500

502

504

500

502

504

600

900

902

904

900

902

904

MINIMALLY INVASIVE COMPLIANT DEVICES FOR TOTAL LUMBAR DISC REPLACEMENT

CROSS-REFERENCE TO RELATED APPLICATIONS

This application claims priority to U.S. Provisional Patent Application Ser. No. 63/457,482 filed on Apr. 6, 2023, entitled "Minimally Invasive, Posteriorly Implantable, Compliant Total Lumbar Disc Replacement," the entire disclosure of which is incorporated herein by reference.

TECHNICAL FIELD

The present disclosure relates generally to minimally invasive compliant devices for total lumbar disc replacement.

BACKGROUND

Total lumbar disc replacement is a surgical procedure performed on patients with severe and consistent pain caused by disc herniations, osteoarthritis, spondylolisthesis, and other spinal pathologies. The procedure involves removing the spinal disc located between two vertebrae and replacing it with a mechanical device that articulates ideally in the same manner as the original disc.

In some cases, a static or rigid cage can be used instead of an articulating device to stabilize the affected spinal segments and lead to spinal fusion. However, fusing two vertebrae together can cause the adjacent vertebral discs to move more than normal, resulting in abnormal motion and increased risk of accelerated degeneration. Additionally, fusion of multiple segments can cause reduction in overall spinal motion which can restrict one's ability to perform normal activities. Therefore, an articulating device is preferred over a static fusion cage to prevent degeneration of adjacent segments.

Existing lumbar disc replacements are relatively large and are implanted from an anterior surgical approach, leading to significant soft tissue damage and long hospital stays. Although spinal surgery has been moving towards minimally invasive approaches, existing articulating disc implants are too large for such a procedure.

As a result, there is need for minimally invasive articulating implant devices for total lumbar disc replacement that may, in some embodiments, be implanted anteriorly or laterally.

BRIEF SUMMARY OF THE DISCLOSURE

One aspect of the present disclosure generally relates to minimally invasive articulating implant devices for total lumbar disc replacement. In particular, the present disclosure relates to spinal implant devices that can be inserted posteriorly, anteriorly, and laterally. Additionally, the present disclosure relates to inverted contact-aided rolling element devices comprising rigid components and flexible components.

According to a first aspect, a spinal disc replacement implant comprising a contact-aided compliant mechanism comprising a first rigid component, a second rigid component, a third rigid component, a first flexible component, a second flexible component, each of the first and second flexible components comprising a first end, a second end, and a third end, the first flexible component disposed between the first rigid component and the second rigid component, the second flexible components disposed between the second rigid component and the third rigid component, the first rigid component further comprising a first bearing surface, wherein the first bearing surface selectively engages an upper bearing surface of the second rigid component, and the third rigid component further comprising a third bearing surface, wherein the third bearing surface selectively engages a lower bearing surface of the second rigid component.

According to a second aspect, the spinal disc replacement implant of the first aspect, wherein the first and second flexible components comprise a substantially V-shape.

According to a third aspect, the spinal disc replacement implant of the first aspect, wherein the first rigid component is positioned parallel to the second rigid component.

According to a fourth aspect, the spinal disc replacement implant of the first aspect, wherein the first rigid component is movable in at least one degree of freedom with respect to the second rigid component.

According to a fifth aspect, the contact-aided compliant mechanism of the first aspect, wherein the first bearing surface extends from one side of the first rigid component toward the second rigid component.

According to a sixth aspect, the spinal disc replacement implant of the fifth aspect, wherein the upper bearing surface extends from one side of the second rigid component toward the first rigid component.

According to a seventh aspect, the spinal disc replacement implant of the fifth aspect, wherein the lower bearing surface extends from one side of the second rigid component toward the third rigid component.

According to an eighth aspect, the spinal disc replacement implant of the first aspect, wherein the third bearing surface extends from one side of the third rigid component toward the second rigid component.

According to a ninth aspect, the spinal disc replacement implant of the first aspect, further including at least one keel.

According to a tenth aspect, the spinal disc replacement implant of the first aspect, wherein at least one of the first, upper, lower, and third bearing surfaces comprises a rounded surface.

According to an eleventh aspect, the contact-aided compliant mechanism of the first aspect, wherein the first rigid component, second rigid component, third rigid component, first flexible component, and second flexible component are manufactured as a single part using 3D printing.

According to a twelfth aspect, the spinal disc replacement implant of the second aspect, wherein the first flexible component is disposed perpendicular to the second flexible component.

According to a thirteenth aspect, the spinal disc replacement implant of the first aspect, wherein the first flexible component comprises a Euler spiral.

According to a fourteenth aspect, the spinal disc replacement implant of the first aspect, wherein the second flexible component comprises a Euler spiral.

According to a fifteenth aspect, the spinal disc replacement implant of the first aspect, wherein the first flexible component has a first stiffness and the second flexible component has a second stiffness.

According to a sixteenth, aspect a spinal disc replacement implant comprising a contact-aided compliant mechanism comprising a first rigid component, the first rigid component including a first bearing surface, a second rigid component, the second rigid component including an upper and lower bearing surface, a third rigid component, the third rigid component including a third bearing surface, a plurality of flexible components, each of the flexible components including a first end, a second end, and a third end, wherein the first end is attached to one of the first, second, or third rigid component and wherein the third end is attached to one of the first, second, or third rigid component, the first bearing surface selectively engaging the upper bearing surface, and the third bearing surface selectively engaging the lower bearing surface.

According to a seventeenth aspect, the spinal disc replacement implant of the sixteenth aspect, wherein at least one of the first, upper, lower, or third bearing surfaces has a rounded contour.

According to an eighteenth aspect, the spinal disc replacement implant of the sixteenth aspect, wherein each of the flexible components further includes a first region disposed between the first end and the second end and a second region disposed between the second end and the third end.

According to a nineteenth aspect, the contact-aided compliant mechanism of the eighteenth aspect, wherein the first region includes a first radius of curvature.

According to a twentieth aspect, the contact-aided compliant mechanism of the eighteenth aspect, wherein the second region includes a second radius of curvature.

DETAILED DESCRIPTION

Figure 1:
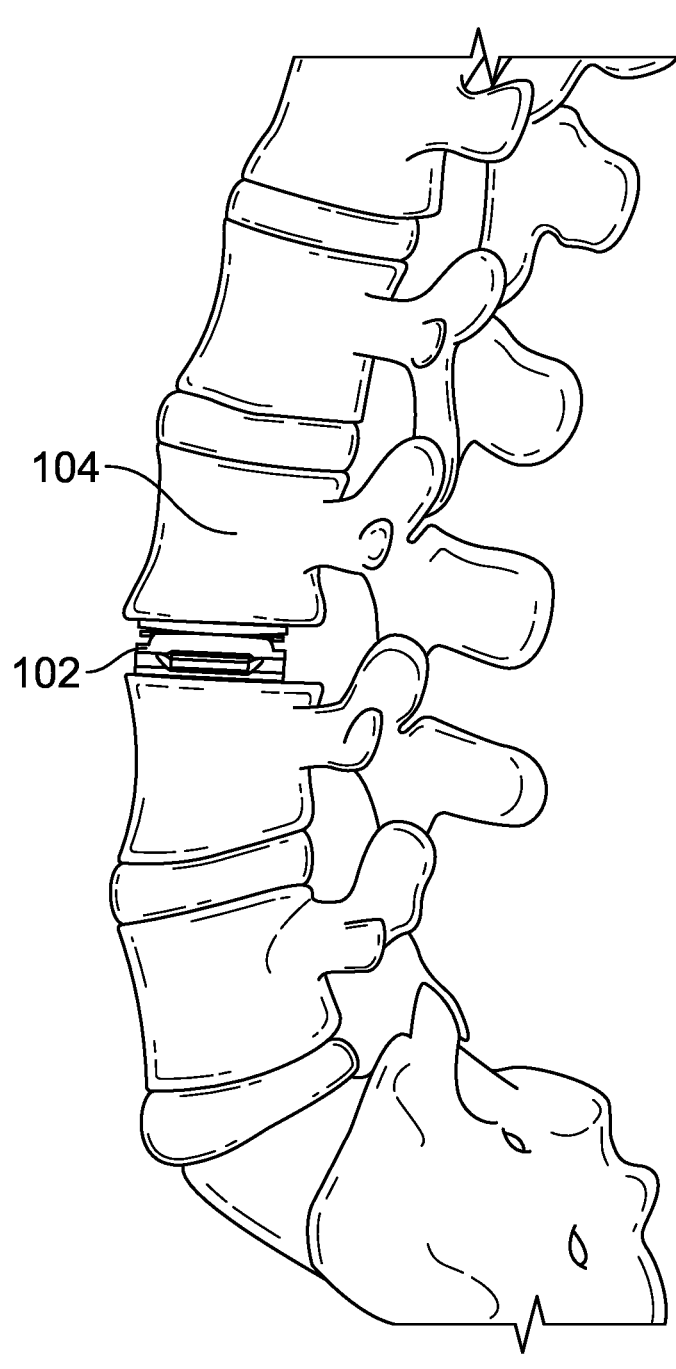
FIG. 1 is a left lateral view of a spine with one posteriorly inserted compliant device placed within for lumbar disc replacement, according to one embodiment.

Whether or not a term is capitalized is not considered definitive or limiting the meaning of a term. As used in this document, a capitalized term shall have the same meaning as an uncapitalized term is intended. However, the capitalization or lack thereof within the remainder of this document is not intended to be necessarily limiting unless the context clearly indicates that such limitation is intended.

Before any embodiments are described in detail, it is to be understood that the disclosure is not limited in its application to the details of construction and the arrangement of components set forth in the following description or illustrated in the following drawings, which is limited only by the claims that follow the present disclosure. The disclosure is capable of other embodiments, and of being practiced, or of being carried out, in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following description is presented to enable a person skilled in the art to make and use embodiments of the disclosure. Various modifications to the illustrated embodiments will be readily apparent to those skilled in the art, and the generic principles herein can be applied to other embodiments and applications without departing from embodiments of the disclosure. Thus, embodiments of the disclosure are not intended to be limited to embodiments shown but are to be accorded the widest scope consistent with the principles and features disclosed herein. The following detailed description is to be read with reference to the figures, in which like elements in different figures have like reference numerals. Skilled artisans will recognize the examples provided herein have many useful alternatives and fall within the scope of embodiments of the disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Utilization of total spinal disc replacement in the lumbar spine is performed less frequently than procedures which completely immobilize the spinal segment for treatment. One factor that contributes to this discrepancy is the lack of existing device solutions that match the biomechanics of a healthy spinal disc. The embodiments of the compliant device described herein more closely mimic the biomechanics of a healthy spine and can be used for total disc replacement. In addition, the compliant device described herein can be inserted into the spine posteriorly, anteriorly, or laterally. Additionally, the compliant device may have vertical compressibility with a high compressible load bearing capability, two degrees of rotational freedom at a tailorable stiffness, a variable center of rotation, and low rolling friction to minimize wear debris.

According to some embodiments, the compliant devices as described herein are designed to have a compact outer profile. In some embodiments, the device can be inserted posteriorly, anteriorly, or laterally without departing from the principles of this disclosure. In various embodiments, the compliant device is designed using contact aide rolling elements. In some embodiments, the device is designed using inverted contact-aided rolling element (ICORE) mechanisms. In some embodiments, the device can be inserted bilaterally from each side of the spinal cord and can provide stability and reduced subsidence due to increased total footprint.

In some embodiments, the compliant device consists of flexible components, which work in tandem with passive rolling joints to achieve controlled forward-backward rotation, lateral rotation, vertical translation, and axial rotation. In additional embodiments, the dimensions and material properties of the flexible components control the stiffness of the device in each of these degrees of freedom. This can allow for the stiffness in each individual axis to be tailored, (e.g., to match the stiffness of a healthy spinal motion segment). In further embodiments, the curvature of the rolling contact points can be tailored to vary the location and orientation of the instantaneous screw axis of the device during motion, (e.g., to match the motion of a certain location on the spine).

The embodiments of the compliant device described herein may to support high compressive loads, but not transmit these forces through the compliant flexures. The properties of the embodiments of the compliant device described herein may mimic the biomechanics of a healthy spinal disc. In alternative embodiments, the compliant device can additionally be used in other replacement devices including but not limited to replacements for the knee, ankle, wrist, and elbow without departing from the principles of this disclosure.

In at least one embodiment, the compliant device can be used alone or in tandem with a surrounding compliant outer shell, which can provide greater disc distraction and device footprint which can minimize device subsidence into the vertebral body.

Overall, the compliant devices described herein can be used as minimally invasive options for total spinal disc replacement and can also reduce soft tissue damage and hospital stay while improving patient outcomes by minimizing device subsidence and adjacent segment degeneration.

Figure 2:
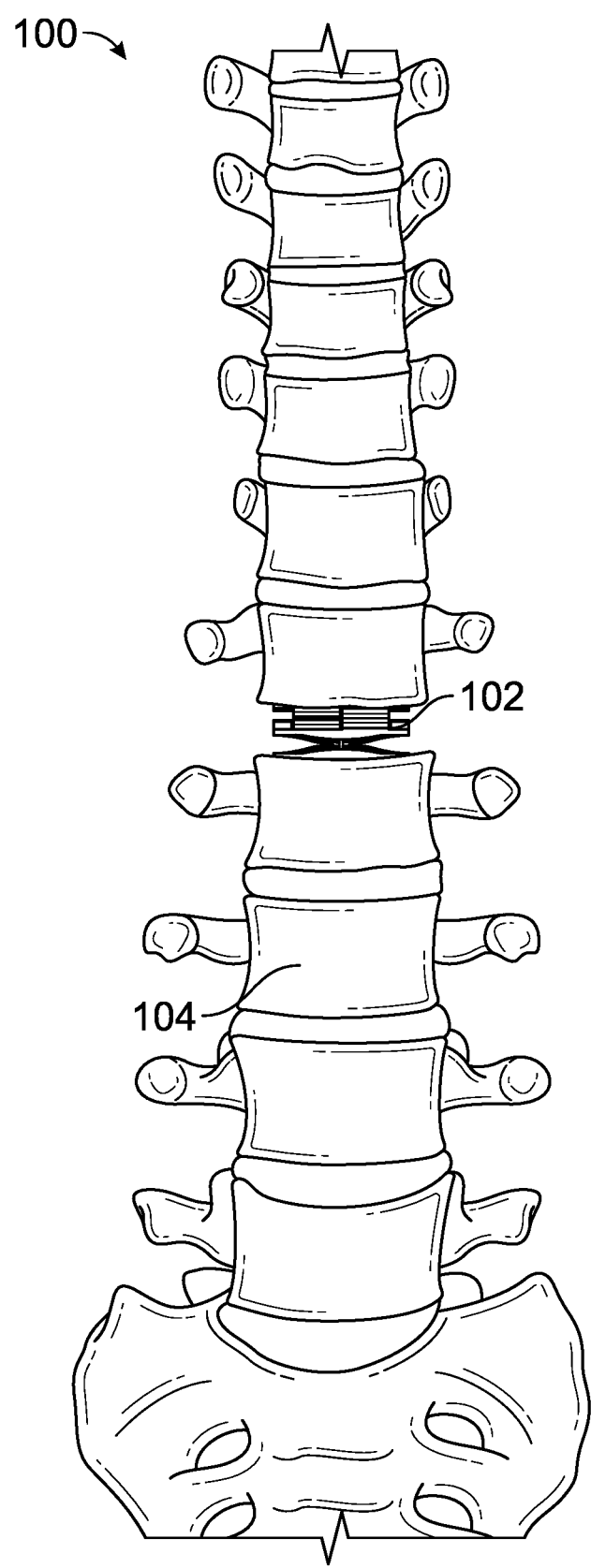
FIG. 2 is an anterior view of a spine with one posteriorly inserted compliant device placed within for lumbar disc replacement, according to one embodiment.
Figure 3:
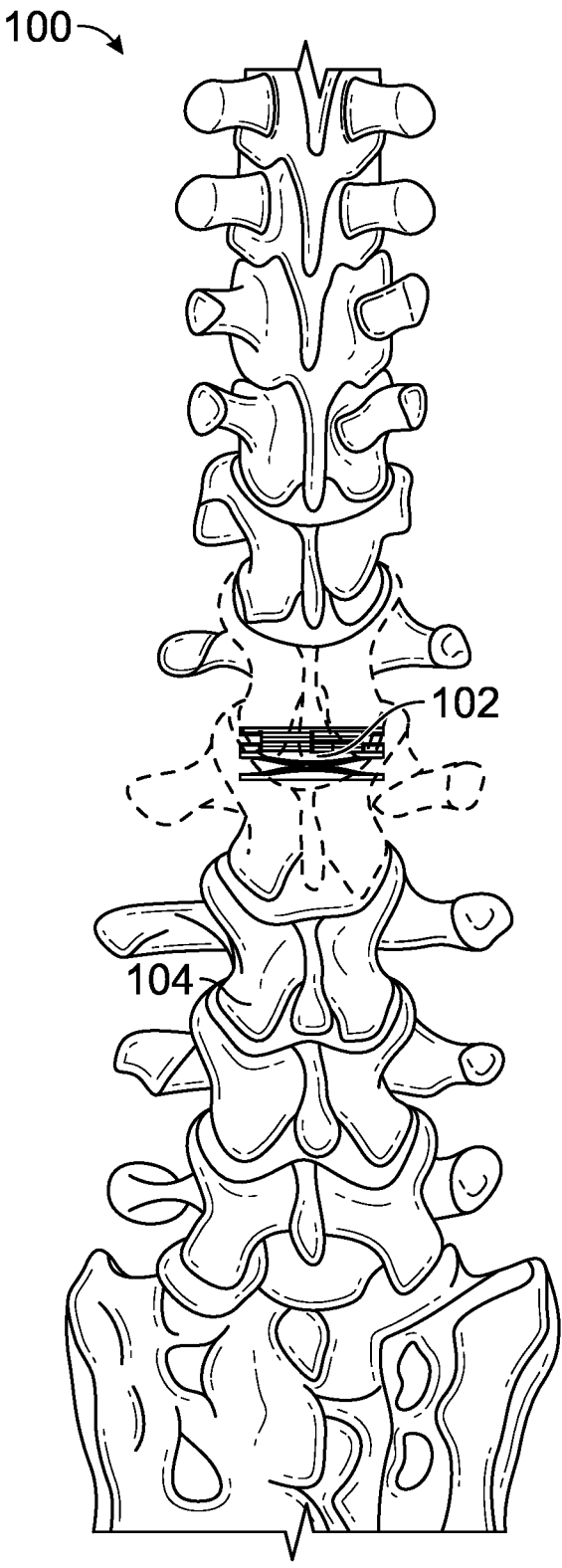
FIG. 3 is a posterior view of a spine with one posteriorly inserted compliant device placed within for lumbar disc replacement, according to one embodiment.

Turning now to FIGS. 1-3, one embodiment of a compliant device 100 in accordance with the principles of this disclosure is shown inserted into a patient's spine 104. In various embodiments, the compliant device 100 includes an implant body 102. In at least one embodiment, the compliant device 100 can be inserted into the spine 104.

In some embodiments wherein the compliant device 100 can be inserted into the spine 104, the compliant device 100 can be inserted posteriorly. In additional embodiments, the compliant device 100 can be inserted into a lumbar region of the spine 104. In various embodiments, the compliant device 100 can be used as a minimally invasive device for total lumbar disc replacement. In some embodiments, the compliant device 100 can be used unilaterally. In alternative embodiments, the compliant device 100 can be used bilaterally. In embodiments when used bilaterally, the compliant device 100 can provide appropriate restorative forces and moments to the spinal segment, which can enable restoration of both the quantity of mechanical motion (e.g., range of motion), as well as the quality of motion (e.g., rotational and translational stiffness).

In some embodiments, the compliant device 100 can be designed to be any interbody device. In some embodiments, the compliant device 100 can be manufactured using additive manufacturing. In a particular embodiment, the additive manufacturing can be 3D printing. In some embodiments, the compliant device 100 can be manufactured as a single piece using additive manufacturing. In additional embodiments, the device 100 can be designed in a patient specific manner.

Figure 4:
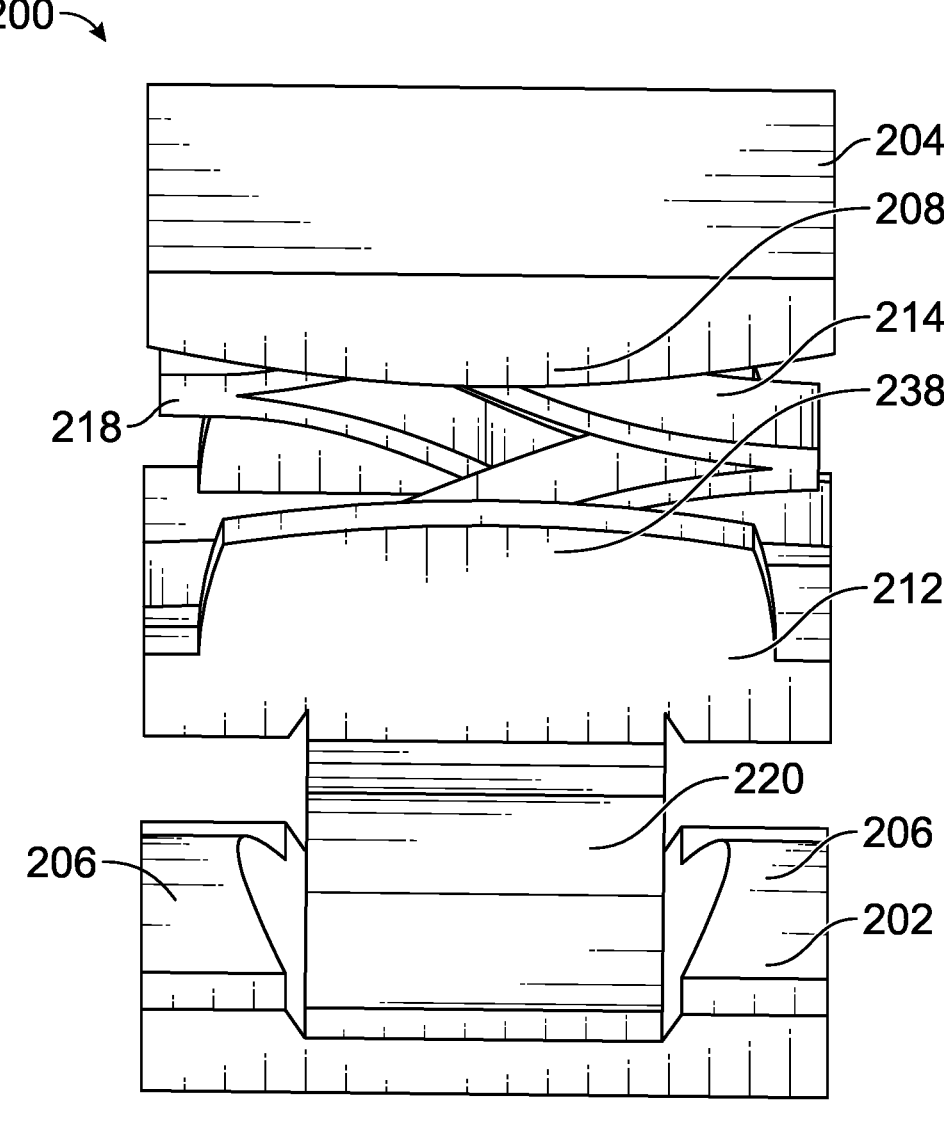
FIG. 4 is a side view of one posteriorly inserted compliant device, according to another embodiment.
Figure 5:
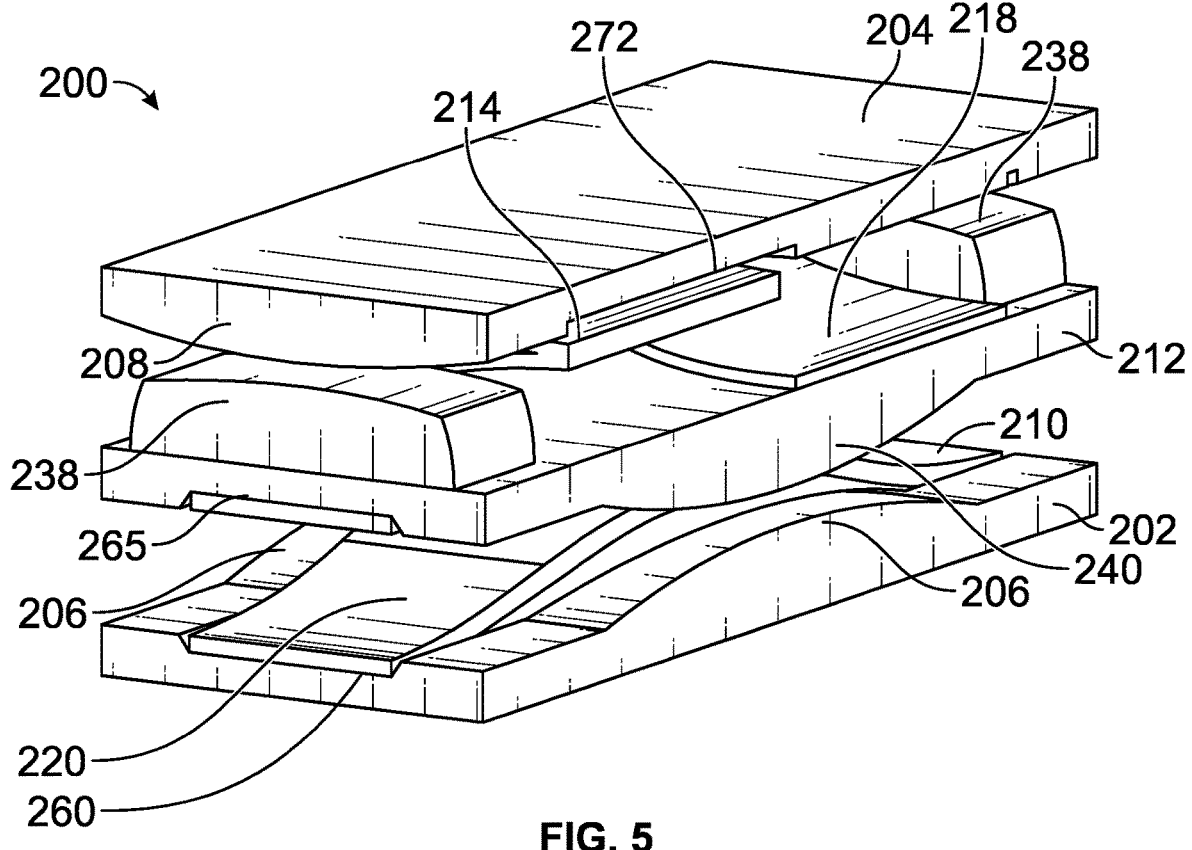
FIG. 5 is a perspective view of the posteriorly inserted compliant device of FIG. 4.

Referring now to FIGS. 4 and 5, one embodiment of a compliant device 200 in accordance with the principles of this disclosure is shown. The compliant device 200 includes a first rigid component 202, a second rigid component 204, a third rigid component 212, a first flexible component 210, a second flexible component 220, a third flexible component 214, and a fourth flexible component 218. In some embodiments, the compliant device 200 may have at least one or two degrees of rotational freedom without departing from the principles of this disclosure. In some embodiments, the compliant device 200 may include initial spacing between the interacting rigid components 202, 204, 212. In some embodiments, the compliant device 200 may include inverted contact-aided rolling element (ICORE) mechanisms. In various embodiments, the compliant device 200 is used as a spinal implant. In an additional embodiment, the device 200 is posteriorly inserted for total lumbar spinal disc replacement.

In one embodiment, the compliant device 200 can include at least the first rigid component 202, the second rigid component 204, and/or the third rigid component 212 may include at least one rounded bearing surface. In various embodiments, the first rigid component 202 can be designed in any suitable shape without departing from the principles of this disclosure. In another embodiment, the first rigid component 202 may include at least two edges with a bearing surface 206 on opposite sides of the first rigid component 202 for contact with the third rigid component 212. In some instances, the bearing surface 206 is rounded.

In various embodiments, the second rigid component 204 can be designed in any shape. In another embodiment, the second rigid component 204 may include at least two edges with a bearing surface 208 on opposite sides of the second rigid component 204 for contact with the third rigid component 212. In some instances, the bearing surface 208 can be rounded.

In multiple embodiments, the third rigid component 212 can be designed in any shape. In another embodiment, the third rigid component 212 may include at least one lower edge with a rounded bearing surface 240 for contact with the first rigid component 202. In additional embodiments, the third rigid component 212 may include at least two edges with a rounded bearing surface 238 on opposite sides of the third rigid component 212 for contact with the second rigid component 204.

In various embodiments, the device 200 can include the rigid components 202, 204, 212 designed to include at least one or several ingresses which are formed to mate around the flexible components 210, 220, 214, 218. In some embodiments, the device 200 may include a first ingress 272, and/or a second ingress (not shown but located opposite 265 on the third rigid component 212). In multiple embodiments, the ingresses can be any shape that allows for the flexible components 210, 220, 214, 218 to fit within.

In additional embodiments, the device 200 can include at least one hollow track perpendicular to the axis of curvature (parallel to the CORE axis of travel) which can house the flexible components (e.g., 210, 220). In some embodiments, the compliant device 200 can include a first hollow track 260 and a second hollow track 265. In some embodiments, the compliant device 200 includes the first hollow track 260 and the second hollow track 265 which can house the first and second flexible components 210, 220.

In some embodiments, the flexible components 210, 220, 214, 218 can be designed in any suitable shape without departing from the principles of this disclosure. In some embodiments, the flexible components 210, 220, 214, 218 can be designed in a substantially V-shape having two regions extending from a vertex. In some embodiments, the shape of the two regions extending from the vertex can have a curvature with a radius of curvature of at least 20 mm, at least 30 mm, at least 60 mm, at least 70 mm. In alternative embodiments, the shape of the two regions extending from the vertex can have can be substantially straight.

In various embodiments, the flexible components 210, 220, 214, 218 may at least partially include a Euler spiral. In yet other embodiments, the shape of the two regions extending from the vertex may be a deployable Euler spiral connector (DESC), which provides improved compressibility for packaging purposes. See U.S. Patent Publication 2022/0047397 incorporated by reference in its entirety.

Figure 7:
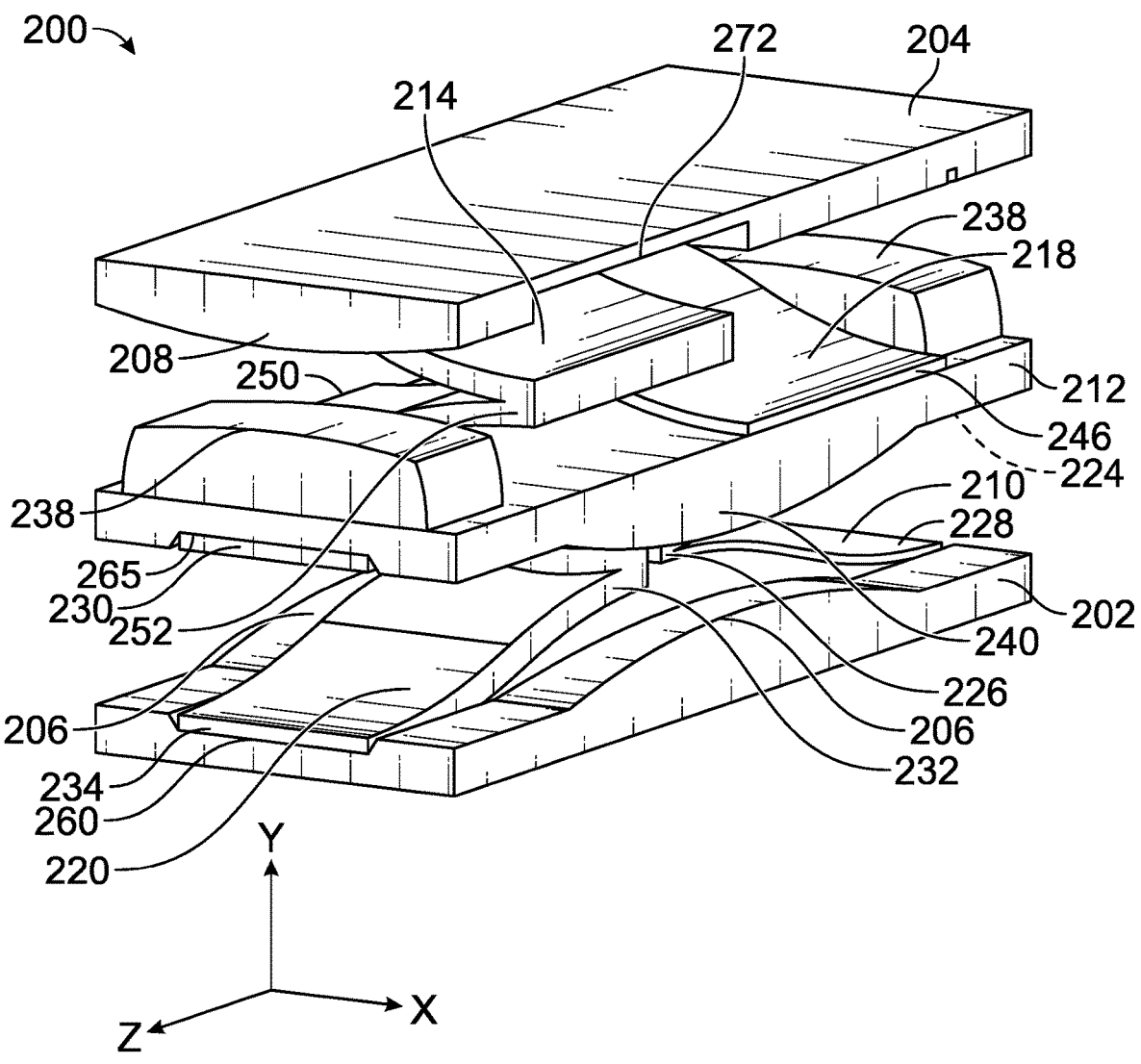
FIG. 7 is a perspective view of the posteriorly inserted compliant device of FIG. 4 in a neutral position, according to one embodiment.

In various embodiments, the flexible components 210, 220, 214, 218 can have a thickness of at least 0.5 mm, 1 mm, 1.5 mm, 2 mm, or 5 mm. In various embodiments, the first flexible component 210 has a width of at least 5 mm, at least 7 mm, at least 14 mm, at least 20 mm. In some embodiments, flexible components 210, 220, 214, 218 may have the same or different thicknesses without departing from the principles of this disclosure. For example, as shown in FIG. 7, flexible component 214 is shown having a greater thickness than flexible component 218. Similarly, flexible component 220 is shown having a greater thickness than flexible component 210. Further, the thicknesses of each flexible component may be variable along the length of each flexible component 210, 220, 214, 218 without departing from the principles of this disclosure.

In various embodiments, the compliant device 200 can be inserted into a spine. In additional embodiments, the compliant device 200 can be used unilaterally or bilaterally. In some embodiments, the compliant device 200 can be inserted posteriorly into the spine. In various embodiments, when used bilaterally, the vertical flex of the device 200 can provide appropriate restorative forces and moments to the spinal segment, which can enable restoration of both the range of mechanical motion, as well as the quality of motion (e.g., rotational and translational stiffness).

Figure 6:
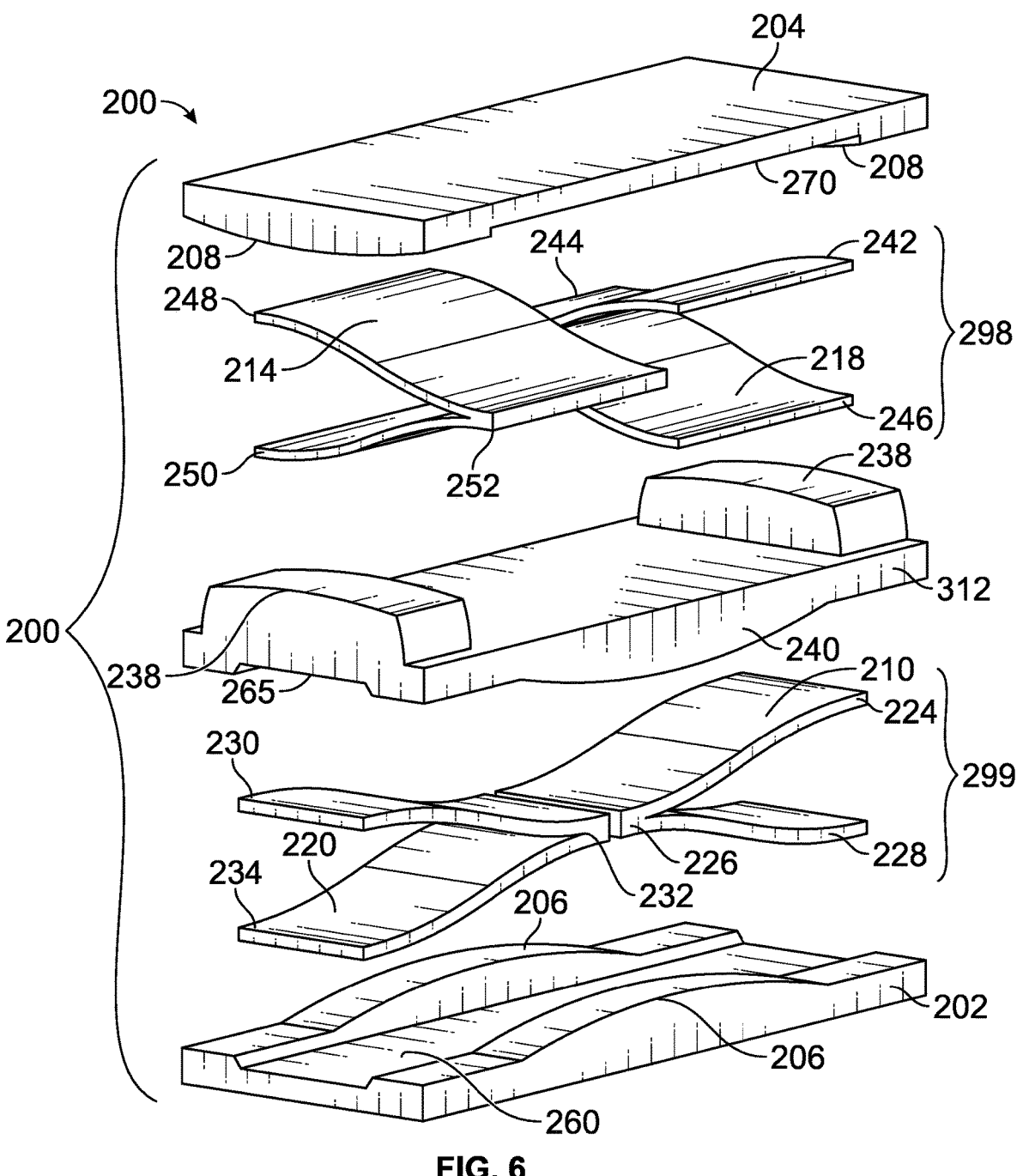
FIG. 6 is an exploded view of the posteriorly inserted compliant device of FIG. 4, according to another embodiment.

Turning to FIG. 6, one embodiment of a compliant device 200 in accordance with the principles of this disclosure is provided. The compliant device 200 includes a first rigid component 202, a second rigid component 204, a third rigid component 212, a first flexible component 210, a second flexible component 220, a third flexible component 214, and a fourth flexible component 218. In some embodiments, the compliant device 200 may have at least one or two degrees of rotational freedom. In some embodiments, the compliant device 200 may include initial spacing in between the interacting rigid components 202, 204, 212.

In various embodiments, the compliant device 200 can include the rigid components 202, 204, 212 designed to include at least one or several features which are formed to mate around the flexible components 210, 220, 214, 218. In some embodiments, the compliant device 200 may include a first feature 270, and/or a second ingress (not shown but located opposite 265 on the third rigid component 212). In multiple embodiments, the features can be any shape that allows for the flexible components 210, 220, 214, 218 to fit therewithin.

In one embodiment, the compliant device 200 can include at least the first rigid component 202, the second rigid component 204, and/or the third rigid component 212 designed to include at least one rounded bearing surface. The first rigid component 202 may include at least one or two rounded bearing surfaces 206 disposed on opposite sides of the first rigid component 202 that make selective contact with lower bearing surfaces 240 disposed on opposite sides of the third rigid component 212.

In various embodiments, the second rigid component 204 can be designed in any suitable shape without departing from the principles of this disclosure. The second rigid component 204 may include at least one or two rounded bearing surfaces 208 disposed on opposite sides of the second rigid component 204 that make selective contact with upper bearing surfaces 238 disposed on opposite sides of the third rigid component 212.

In multiple embodiments, the third rigid component 212 can be designed in any suitable shape without departing from the principles of this disclosure. In another embodiment, the third rigid component 212 may include at least one lower rounded bearing surface 240 for making selective contact with bearing surfaces 206 disposed on opposite sides of the first rigid component 202. In additional embodiments, the third rigid component 212 may include at least one or two upper rounded bearing surfaces 238 disposed on opposite sides of the third rigid component 212 for making selective contact with the bearing surfaces 208 disposed on opposite sides of second rigid component 204.

Figure 8:
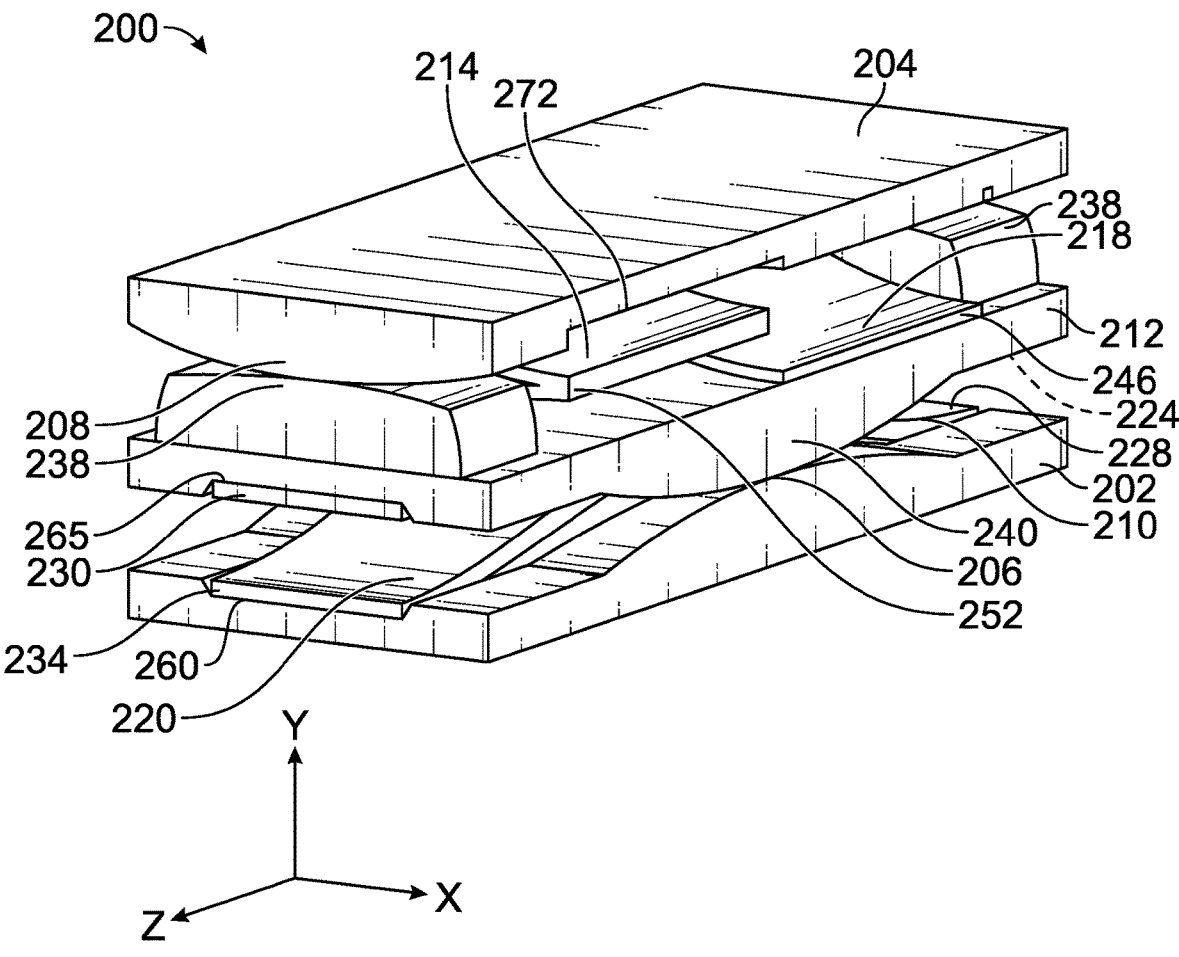
FIG. 8 is a perspective view of the posteriorly inserted compliant device of FIG. 4 in a vertically compressed position, according to one embodiment.
Figure 9:
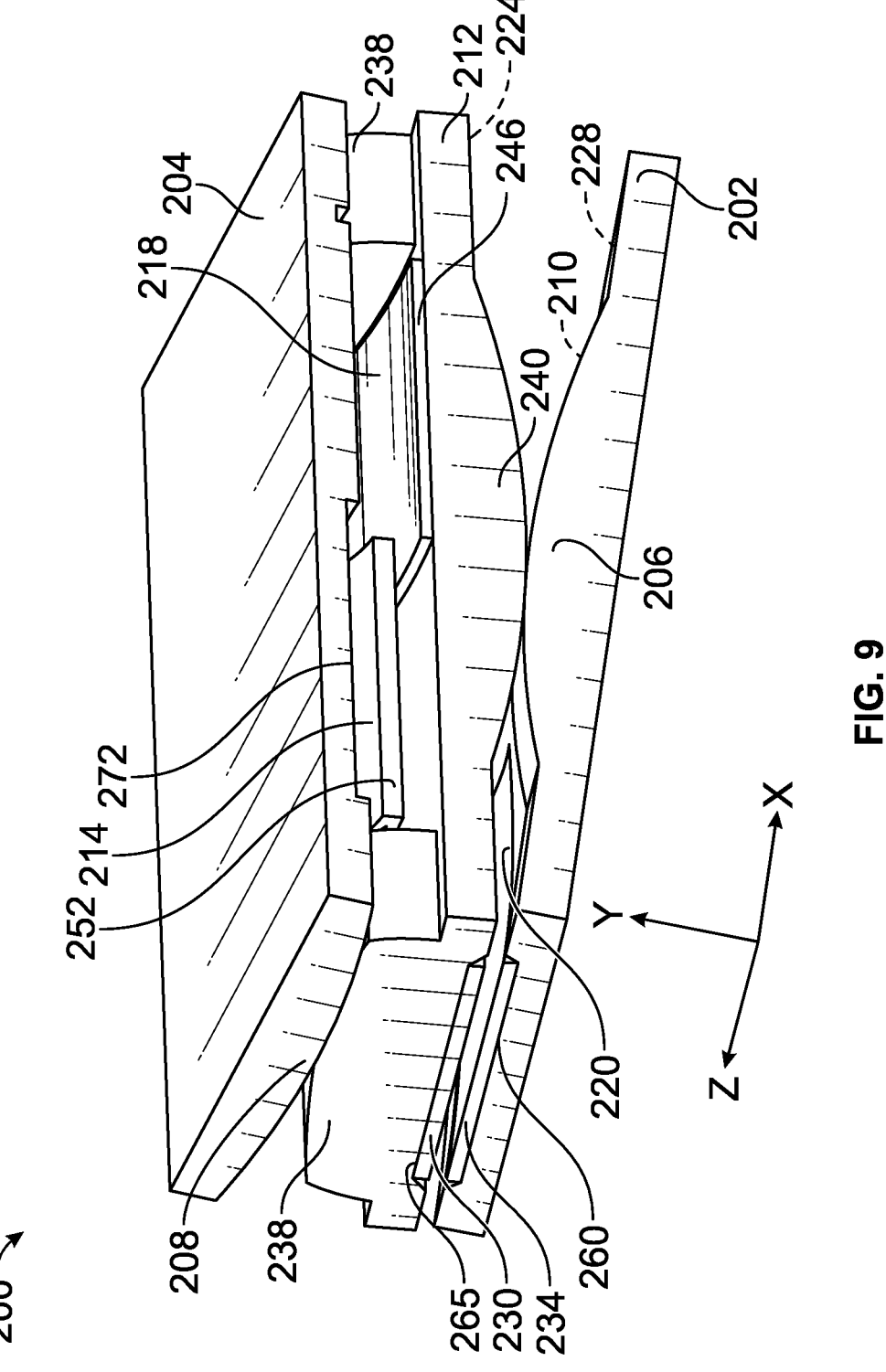
FIG. 9 is a perspective view of the posteriorly inserted compliant device of FIG. 4 in a vertically compressed and rotated position, according to one embodiment.

In multiple embodiments of the compliant device 200 the first rigid component 202 may be a lowermost rigid body with at least one or two rounded bearing surface 206 which can control the rotation about the x axis (See FIGS. 7-9). In various embodiments of the compliant device 200, the first and second flexible components 210, 220 can allow for rotation about the x axis (See FIGS. 7-9). In multiple embodiments of the compliant device 200 the third rigid component 212 may be a middle rigid body comprising at least one lower rounded bearing surface 240 which can control the x axis rotation and at least one or two upper rounded bearing surfaces 238 of the third rigid component 212 which can control the z axis rotation (See FIGS. 7-9). In some embodiments, the third and fourth flexible components 214, 218 can allow for rotation about the z axis (See FIGS. 7-9). In additional embodiments, the second rigid component 204 may be an uppermost rigid body with at least one or two rounded bearing surfaces 208 which can control rotation about the z axis (See FIGS. 7-9).

In some embodiments of device 200, the first flexible component 210 can include a first end 224, a second end 226, and a third end 228, wherein the second flexible component 210 is V-shaped and the second end 226 is the vertex. In various embodiments of device 200, the second flexible component 220 can include a first end 230, a second end 232, and a third end 234, wherein the second flexible component 220 is V-shaped and the second end 232 is the vertex. In multiple embodiments, the third flexible component 214 can include a first end 248, a second end 252, and a third end 250, wherein the second flexible component 214 is V-shaped and the second end 252 is the vertex. In yet another embodiment, the fourth flexible component 218 can include a first end 242, a second end 244, and a third end 246, wherein the fourth flexible component 218 is V-shaped and the second end 244 is the vertex.

In various embodiments of the compliant device 200 the first and second flexible components 210, 220 can be positioned in an INT-CORE configuration wherein the first and second flexible components 210, 220 can be positioned in line with each other wherein the second ends 226, 232 are positioned adjacent to each other and the first and third ends 224, 228, 230, 234 are positioned at opposite sides of the compliant device 200. In additional embodiments, the third and fourth flexible components 214, 218 can also be oriented in an INT-CORE configuration. In various embodiments, the INT-CORE configuration can include a structure with multiple half-traversal flexible components.

In additional embodiments, the compliant device 200 can include at least one hollow track perpendicular to the axis of curvature (parallel to the INT-CORE axis of travel) which can house the flexible components (e.g., 210, 220). In some embodiments, the compliant device 200 can include a first hollow track 260 and a second hollow track 265. In some embodiments, the compliant device 200 includes the first hollow track 260 and the second hollow track 265 which can house the first and second flexible components 210, 220. In various embodiments, the advantages of the INT-CORE configuration over other mechanisms and/or configuration can include improved space utilization, avoidance of pinching of the flexures between the rolling contact surfaces, and increased case of manufacturing.

In multiple embodiments of the compliant device 200 the first and second flexible components 210, 220 can be positioned in an INV-CORE configuration wherein the first and second flexible components 210, 220 can be positioned in parallel with each other wherein the second ends 226, 232 are positioned opposite sides of the compliant device 200 and the first and third ends 224, 228, 230, 234 are positioned on opposite sides of the compliant device 200. In additional embodiments, the third and fourth flexible components 214, 218 can also be oriented in an INV-CORE configuration. In various embodiments, the INV-CORE configuration can include a structure with multiple traversal flexible components.

In various embodiments, the INV-CORE configuration can include rolling features to the lateral edges with the flexible components 214, 218 placed in the central body of the mechanism. In some embodiments, the advantages of the INV-CORE configuration in device 200 over other mechanisms and/or configuration can include tailorable curvature of the rolling contact surface, mechanical stiffness determined by the mechanical properties of the material and the dimensions of the connecting flexural elements), which can avoid pinching the flexures themselves between the rolling contact surfaces. Additionally in some embodiments of device 200, the INV-CORE configuration can allow the flexible components to be used as compliant springs which can support loading of the surface prior to contact between the rolling contact surfaces, which can yield capability for the INV-CORE configuration to provide tailored force-displacement stiffness response along the axes.

In yet another alternative embodiment, flexible components 210, 220 and/or 214, 218 can be positioned wherein the second ends 226, 232, 244, 252, are at the same side of the compliant device 200 and the first ends 224, 230, 242, 248 and third ends 228, 234, 246, 250 are at the other side of the device.

In other embodiments, the compliant device 200 can include an upper portion 298 and a lower portion 299. In various embodiments and as shown in FIG. 6, the compliant device 200 can include the upper portion 298 of at least two flexible components 214, 218 configured in an INV-CORE configuration and the lower portion 299 of at least two flexible components 210, 220 configured in an INT-CORE configuration. In some embodiments, the flexible components 218 of the upper portion 298 may control the rotation about the Z-axis and the flexible components 210, 220 of the lower portion 299 may control the rotation about the X-axis. In multiple embodiments, both the upper portion 298 and the lower portion 299 may include at least two sets of flexible components to connect the rigid components and provide expansion in the y-direction.

In various embodiments (and as shown in FIG. 6) the compliant device 200 can comprise flexible components in the upper portion 298 configured in an INV-CORE configuration and flexible components in the lower portion 299 configured in an INT-CORE configuration. In alternative embodiments, the compliant device 200 can comprise the flexible components 214, 218 of the upper portion 298 configured in an INT-CORE configuration and the flexible components 210, 220 of the lower portion 299 configured in an INV-CORE configuration. In yet another embodiment, the compliant device 200 can be designed where the flexible components in both the upper portion 298 and the lower portion 299 are configured in the same configuration (INV-CORE or INT-CORE) without departing from the principles of this disclosure.

In some embodiments, the compliant device 200 can be used as a spinal disc replacement implant. In some embodiments, the compliant device 200 is comprised of two or more INV-CORE and/or INT-CORE configurations stacked with a 90-degree rotation relative to each other.

In some embodiments, the compliant device 200 may be comprised of two or more INV-CORE and/or INT-CORE configurations stacked with any suitable configuration including, but not limited to a 90-degree rotation relative to each other or any other angle of rotation without departing from the principles of this disclosure. In some embodiments, an alternative configuration of the components may allow for the mechanism to avoid movement in a particular region of space, creating a region of avoidance.

In some embodiments, a compliant device 200 with a configuration of a stacked INV-CORE and/or a stacked INT-CORE configuration can be used in an implant which can provide advantages to the implant. In one embodiment, for a device and/or implant with a non-uniform aspect ratio, the INV-CORE configuration may be preferred for the orientation where the rolling bearing surfaces have a rolling path is along the short axis and the INT-CORE configuration is preferred for the orientation where the rolling bearing surfaces have a rolling path along the long-axis. In many embodiments wherein the device contains a stacked INV-CORE and/or a stacked INT-CORE configuration, the combined configuration yields an optimized combination of mechanical support and flexibility.

Referring now to FIGS. 7-9, one embodiment of the compliant device 200 in various positions is provided. FIGS. 7-9 show the actuation of the compliant device 200 from completely neutral, to compressed vertically, to compressed and rotated. In some embodiments, rotation can occur without compression. In some embodiments, when the compliant device 200 is compressed, the curvature of the contact surfaces can control the rotation pathway and changes in the orientation and location of the instantaneous screw axis. In additional embodiments, when the compliant device 200 is not fully compressed, the stiffness and orientation of the flexible components 210, 214, 218, 220 control the orientation and axis of the instantaneous screw axis.

As shown in FIG. 7, in some embodiments, the compliant device 200 can hold a neutral position wherein there is a maximal amount of space between the rigid components 202, 204, 212. In some embodiments, the compliant device 200 can be designed so that in the neutral position, the first and second rigid components 202, 204 are parallel. In additional embodiments, the flexible components can be manufactured wherein the neutral position of the first and second rigid components 202, 204 could be angled in any number of ways. In various embodiments, the compliant device 200 as used in a spinal implant may include a default rotation about the X-axis as it is determined, to allow for a natural lordotic curvature of the spine.

As shown in FIG. 8, in multiple embodiments, the compliant device 200 can also be vertically compressed along a y axis wherein the amount of space between the rigid components 202, 204, 212 is compressed along the y axis and the rigid components 202, 204, 212 make contact with one another via the rounded contact points. In various embodiments, the flexible components 210, 220, 214, 218 can compress and allow for rolling contact to control the motion and/or rotation of the compliant device 200.

In another embodiment of the compliant device 200, upon vertical compression the at least one or two rounded bearing surfaces 206 of the first rigid component 202 on opposite sides of the first rigid component 202 can make contact with the third rigid component 212 at the at least one lower rounded bearing surface 240 of the third rigid component 212. In some embodiments of the compliant device 200, upon vertical compression the at least two edges with a rounded bearing surface 208 of the second rigid component 204 on opposite sides of the second rigid component 204 can make contact with the third rigid component 212 at the at least one upper edge with an upper rounded bearing surface 238 of the third rigid component 212.

As shown in FIG. 9, in some embodiments, the compliant device 200 can also be compressed along a y axis as well as rotated along the z and or x axis. In various embodiments, the compliant device 200 can be designed wherein the top and bottom regions of the compliant device 200 can roll in their respective axes. As described in FIG. 6, in multiple embodiments of the compliant device 200 the first rigid component 202 may be a lowermost rigid body with at least one or two rounded bearing surfaces 206 which can control the rotation about the x axis. In various embodiments of the device, the first and second flexible components 210, 220 can allow for rotation about the x axis. In multiple embodiments of the compliant device 200 the third rigid component 212 may be a middle rigid body comprising at least one lower rounded bearing surface 240 which can control the x axis rotation and at least one or two upper rounded bearing surfaces 238 of the third rigid component 212 which can control the z axis rotation. In some embodiments, the third and fourth flexible components 214, 218 can allow for rotation about the z axis. In additional embodiments, the second rigid component 204 may be an uppermost rigid body with at least one or two rounded bearing surfaces 208 which can control rotation about the z axis (See FIGS. 7-9). In various embodiments, the motion of the compliant device 200 can be tightly controlled by designing the compliant device 200 using features that would stop the device from rotating beyond a certain point.

In various embodiments, at least two of the compliant device 200 can be inserted bilaterally in a similar surgical approach to the surgical approach for a minimally invasive posterior lumbar fusion procedure. In alternative embodiments, the compliant device 200 can be inserted unilaterally.

In some embodiments, because the compliant device 200 is not static, insertion of the compliant device 200 can be done using a minimally invasive total lumbar disc replacement rather than a fusion. In some embodiments, at least one of the compliant device 200 can be inserted alone. In alternative embodiments, the at least one of the compliant device 200 can be implanted in tandem with any outer cage since the compliant device 200 can be size-constrained by surgical window size. In various embodiments, the outer cage can be any cage that can be implanted into the intervertebral space and expand both laterally and vertically. In some embodiments, the outer cage is an expanding outer cage. In various embodiments the expanding outer cage can be a triaxial expanding interbody device. In alternative embodiments, the outer cage is the outer piece of a posterior inter body fusion system, such as the Flare Hawk spinal fusion device by Integrity Implants.

In various embodiments, at least one of the compliant device 200 may be inserted with an outer expandable cage which can provide the benefit of added expandability and the disc replacement can potentially be revised to a fusion procedure with minimal hardware removal. In some embodiments of device 200 insertion, this can be achieved if the outer expanding piece is fixed to the vertebrae, while the inner actuating piece is made to be removable and can be replaced with a static insert (e.g., revision to a fusion), or with a replacement spinal disc device with equal or different mechanical properties (e.g., an identical device).

In some embodiments, the compliant device 200 can be designed to be any interbody device. In some embodiments, the compliant device 200 can be manufactured using additive manufacturing. In a particular embodiment, the additive manufacturing can be 3D printing. In some embodiments, the compliant device 200 can be manufactured as a single piece using additive manufacturing. In additional embodiments, the device 200 can be designed in a patient specific manner.

Figure 10:
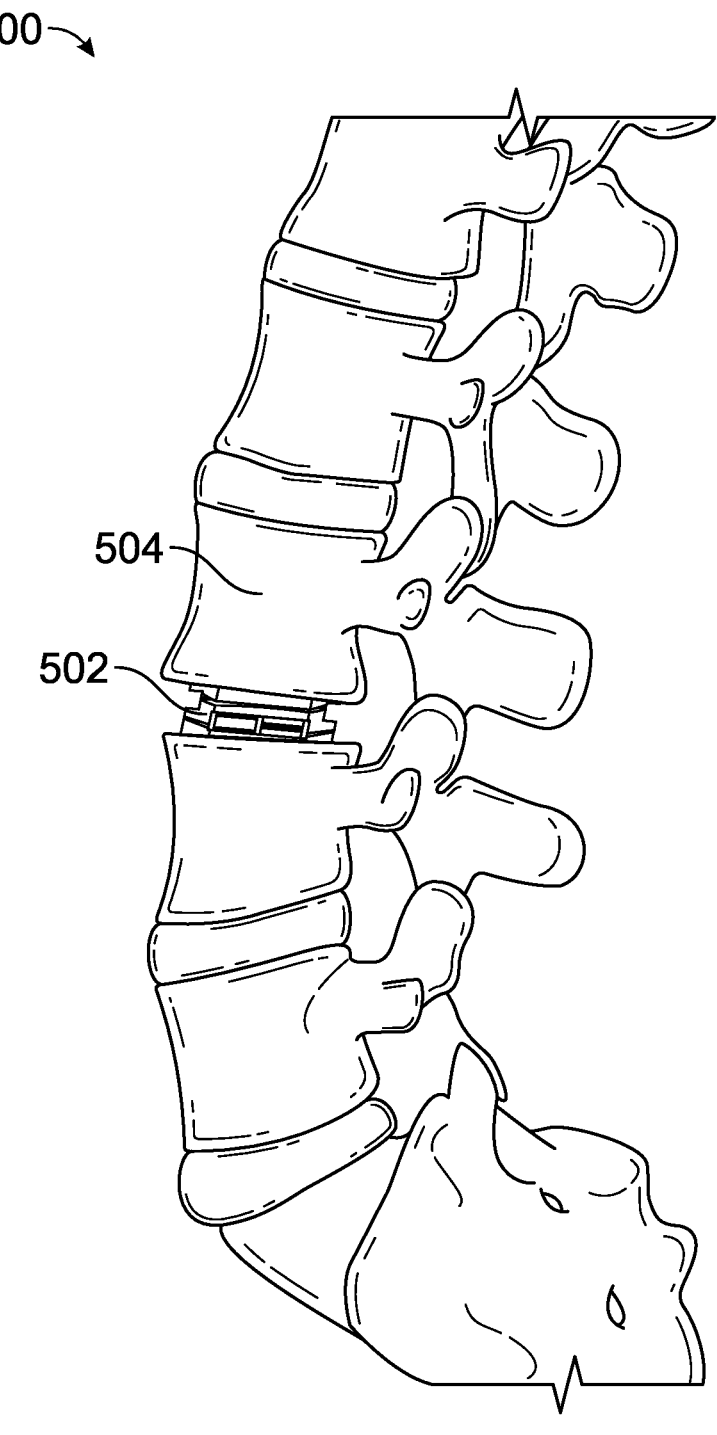
FIG. 10 is a left lateral view of a spine with one anteriorly inserted compliant device placed within for lumbar disc replacement, according to one embodiment.
Figure 11:
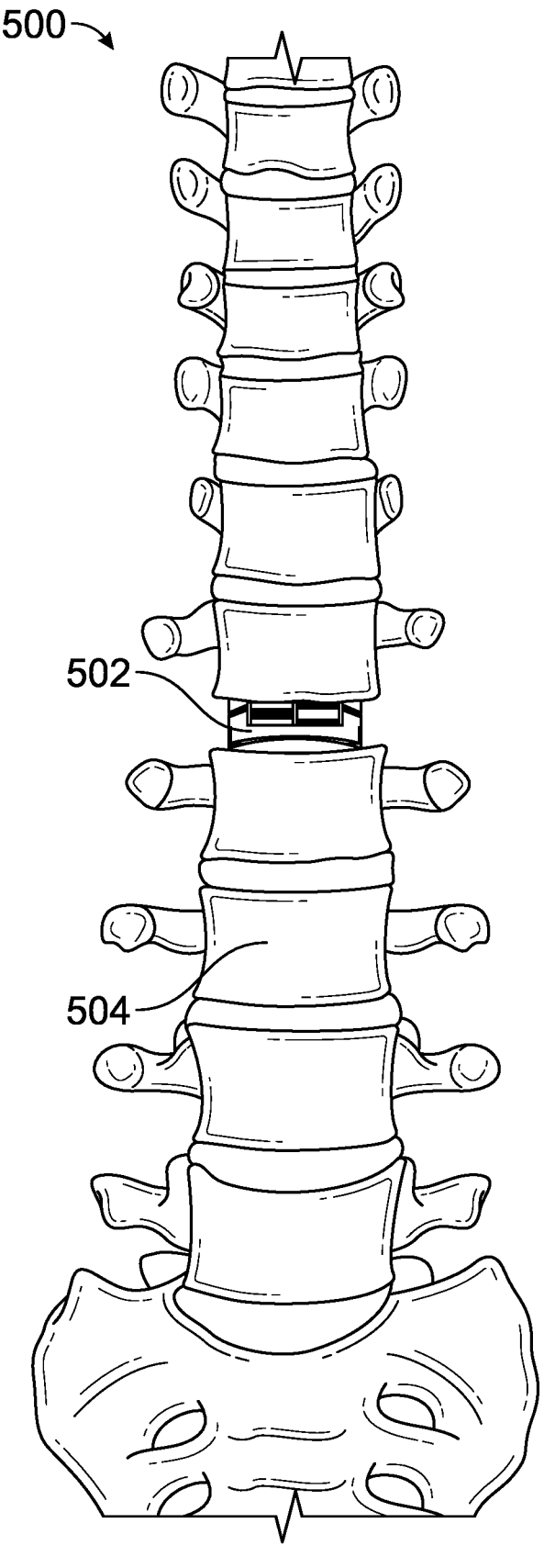
FIG. 11 is an anterior view of a spine with one anteriorly inserted compliant device placed within for lumbar disc replacement, according to one embodiment
Figure 12:
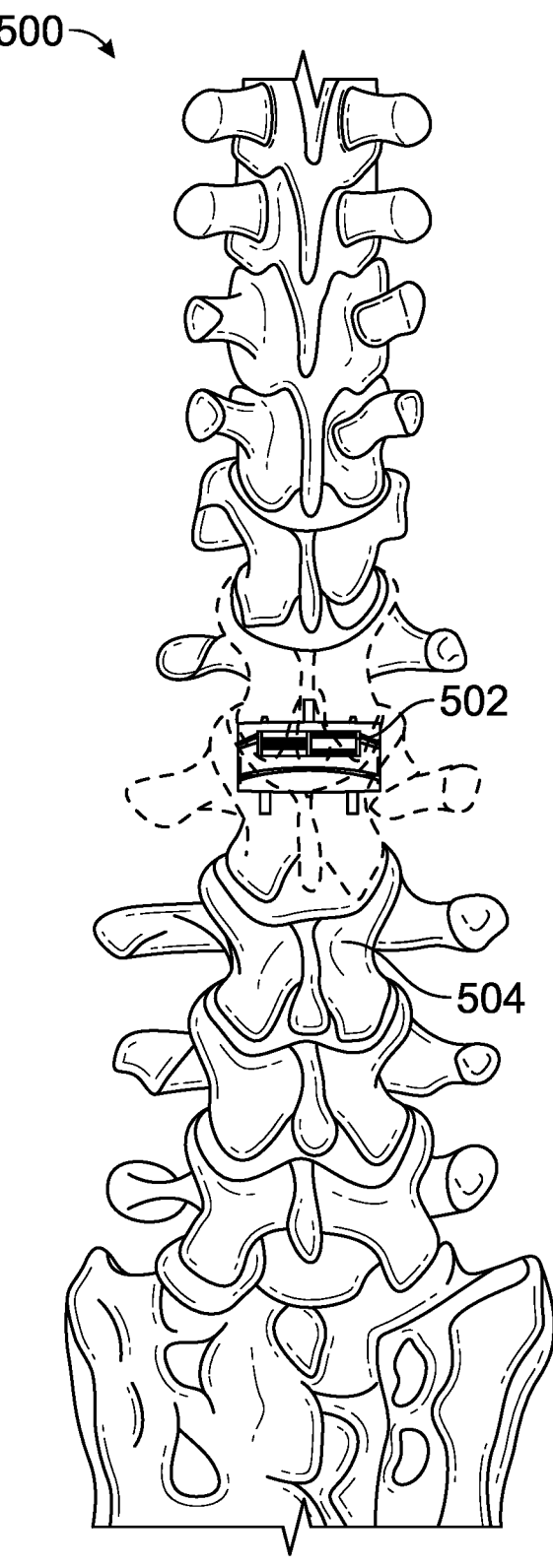
FIG. 12 is a posterior view of a spine with one anteriorly inserted compliant device placed within for lumbar disc replacement, according to one embodiment

Turning now to FIGS. 10-12, one embodiment of a compliant device 500 in accordance with the principles of this disclosure is shown inserted into a spine 504. In various embodiments, the compliant device 500 includes an implant body 502. In at least one embodiment, the compliant device 500 can be inserted into the spine 504. In alternative embodiments, the compliant device 500 can be inserted into a knee, ankle, wrist, elbow, or any other suitable joint or anatomic structure of a human or other animal.

In some embodiments wherein the compliant device 500 can be inserted into the spine 504, the compliant device 500 can be inserted anteriorly. In additional embodiments, the compliant device 500 can be inserted into a lumbar region of the spine 504. In various embodiments, the compliant device 500 can be used as a minimally invasive device for total lumbar disc replacement. In some embodiments, the compliant device 500 can be used unilaterally. In alternative embodiments, the compliant device 500 can be used bilaterally. In embodiments when used bilaterally, the compliant device 500 can provide appropriate restorative forces and moments to the spinal segment, which can enable restoration of both the range of mechanical motion, as well as the quality of motion (e.g., rotational and translational stiffness).

In some embodiments, the compliant device 500 can be designed to be any interbody device. In some embodiments, the compliant device 500 can be manufactured using additive manufacturing. In a particular embodiment, the additive manufacturing can be 3D printing. In some embodiments, the compliant device 500 can be manufactured as a single piece using additive manufacturing. In additional embodiments, the device 500 can be designed in a patient specific manner.

Figure 13:
FIG. 13 is a side view of one anteriorly inserted compliant device, according to another embodiment.
Figure 13:
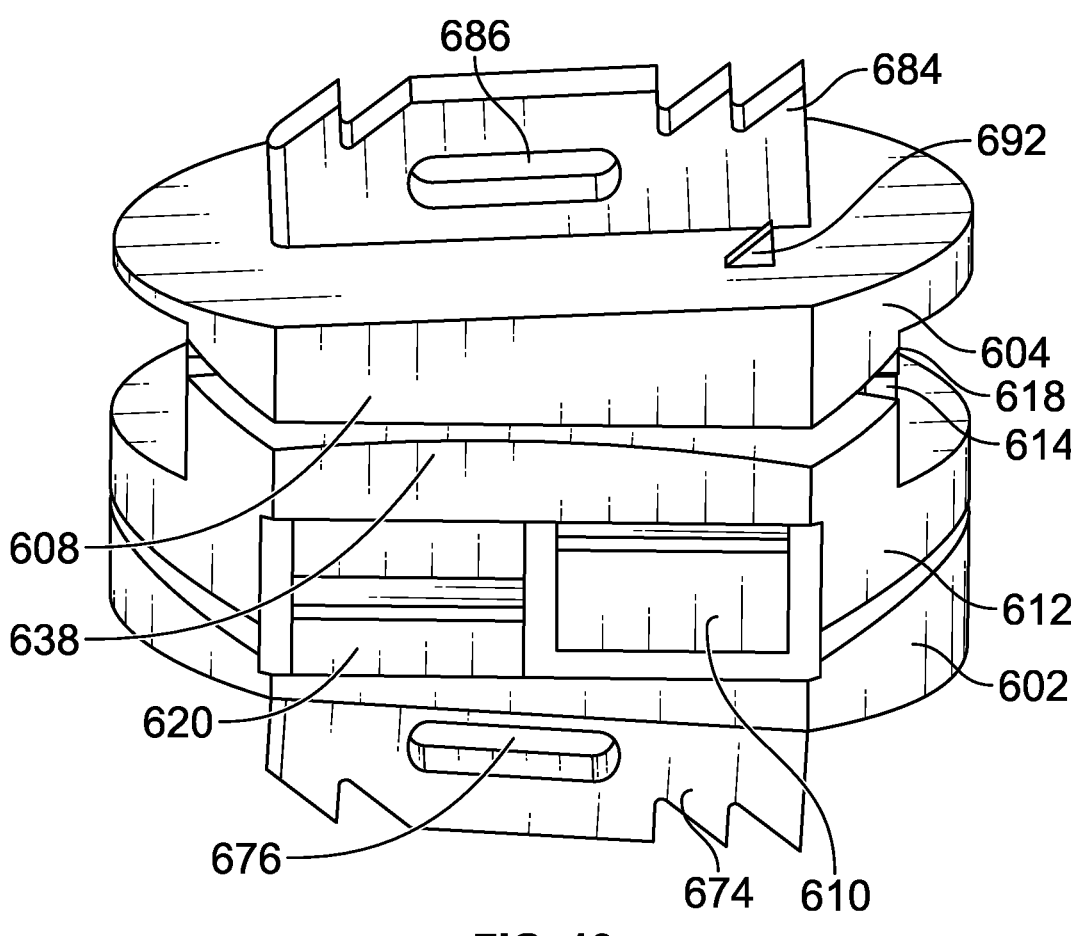
Figure 14:
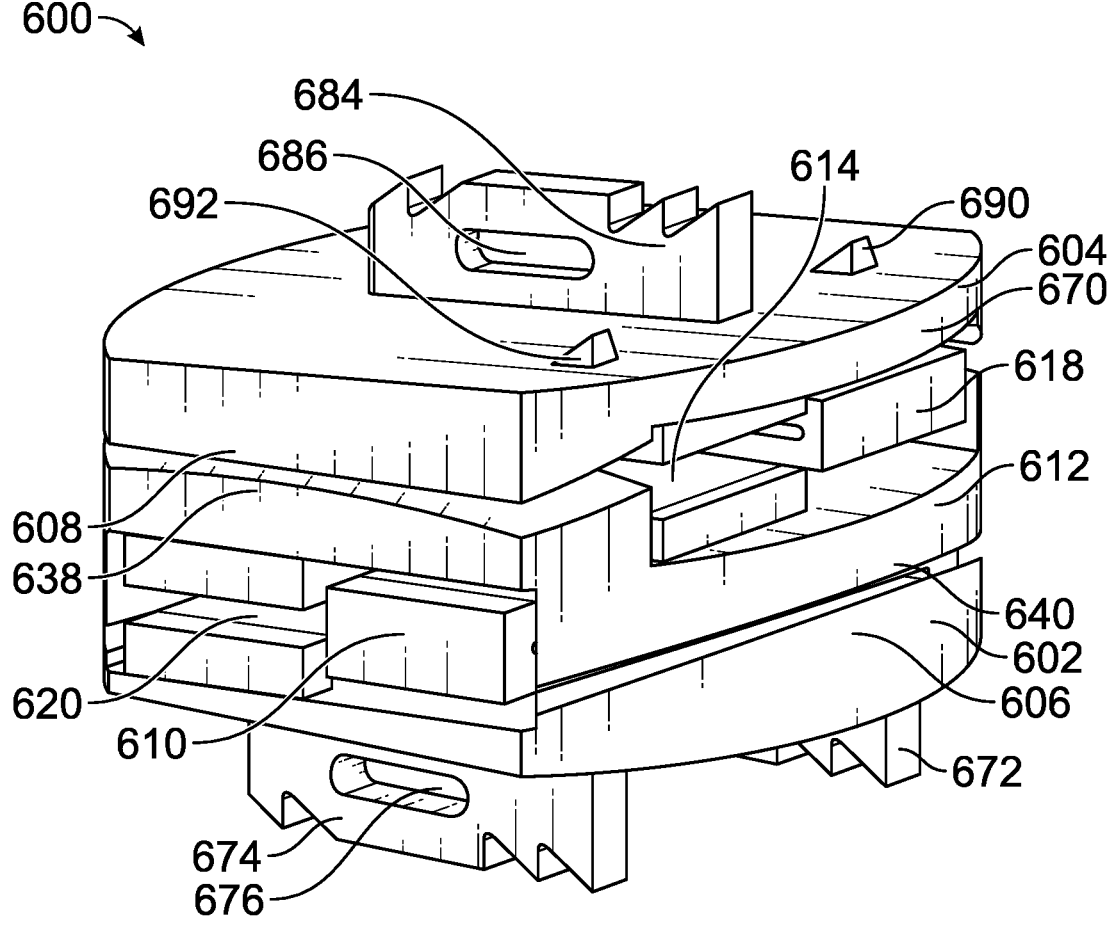
FIG. 14 is a perspective view of the anteriorly inserted compliant device of FIG. 13.

Turning to FIGS. 13 and 14, one embodiment of a compliant device 600 in accordance with the principles of this disclosure is provided. The compliant device 600 includes a first rigid component 602, a second rigid component 604, a third rigid component 612, a first flexible component 610, a second flexible component 620, a third flexible component 614, and a fourth flexible component 618. In multiple embodiments, the compliant device 600 may have at least one or two degrees of rotational freedom. In some embodiments, the compliant device 600 may include initial spacing in between the interacting rigid components 602, 604, 612. In various embodiments, the compliant device 600 is designed using inverted contact-aided rolling element (ICORE) mechanisms. In various embodiments, the compliant device 600 is used as a spinal implant. In an additional embodiment, the compliant device 600 is anteriorly inserted for total lumbar spinal disc replacement.

In one embodiment, the compliant device 600 can include at least the first rigid component 602, the second rigid component 604, and/or the third rigid component 612 designed to include at least one rounded bearing surface. In various embodiments, the first rigid component can be designed in any shape. In another embodiment, the first rigid component 602 may include at least two bearing surfaces 606 on opposite sides of the first rigid component 602 for contact with the third rigid component 612.

In various embodiments, the second rigid component 604 can be designed in any shape. In another embodiment, the second rigid component 604 may include at least two bearing surfaces 608 on opposite sides of the second rigid component 604 for contact with the third rigid component 612.

In multiple embodiments, the third rigid component 612 can be designed in any shape. In another embodiment, the third rigid component 612 may include at least one or two lower rounded bearing surfaces 640 for contact with the first rigid component 602. In additional embodiments, the third rigid component 612 may include at least one or two upper rounded bearing surfaces 638 on opposite sides of the third rigid component 612 for contact with the second rigid component 604.

In various embodiments, the compliant device 600 can optionally include fixation structures. In some embodiments, the fixation structure may be keels or spikes or any other suitable structure to hold the implant in place. In some embodiments, the device includes at least one keel. In alternative embodiments, the device includes at least one keel with a hole. In various embodiments, the at least one keel can be shaped in any shape. In various embodiments, the at least one keel can be shaped in a jagged or spiked shape. In some embodiments the compliant device 600 can include a first keel 672, a second keel 674, and a third keel 684. In additional embodiments, the first keel 672 may include a first hole (not shown). In another embodiment, the second keel 674 includes a second hole 676. In a further embodiment, the third keel 684 can include a third hole 686. Additionally, the compliant device 600 may include at least one or at least two friction structures. In some embodiments, the friction structures may be any shape. In other embodiments, the friction structures may be triangle, cone shaped, spike shaped, or any other suitable shape. Some embodiments of the compliant device 600 may include a first friction structure 690 and a second friction structure 692.

In some embodiments, the flexible components 610, 620, 614, 618 can be designed in any shape. In various embodiments, the flexible components 610, 620, 614, 618 can be designed in a V-shape having two regions extending from a vertex. In some embodiments, the shape of the two regions extending from the vertex can have a curvature with a radius of curvature of at least 20 mm, at least 30 mm, at least 60 mm, at least 70 mm. In alternative embodiments, the shape of the two regions extending from the vertex can have can be substantially straight.

In various embodiments, the flexible components 610, 620, 614, 618 may be configured having a Euler spiral. In yet other embodiments, the shape of the two regions extending from the vertex of the flexible components 610, 620, 614, 618 may be a deployable Euler spiral connector (DESC), which provides maximum compressibility for packing purposes See U.S. Patent Publication 2022/0047397 incorporated by reference in its entirety.

In various embodiments, the flexible components 610, 620, 614, 618 has a thickness of at least 0.5 mm, 1 mm, 1.5 mm, 2 mm, or 5 mm. In various embodiments, flexible components 610, 620, 614, 618 has a width of at least 5 mm, at least 7 mm, at least 14 mm, at least 20 mm In various embodiments, the compliant device 600 can be inserted into a spine. In additional embodiments, the compliant device 600 can be used unilaterally or bilaterally. In some embodiments, the compliant device 600 can be inserted anteriorly into the spine. In various embodiments, when used bilaterally, the vertical flex of the compliant device 600 can provide appropriate restorative forces and moments to the spinal segment, which can enable restoration of both the quantity of mechanical motion (e.g., range of motion), as well as the quality of motion (e.g., rotational and translational stiffness).

Figure 15:
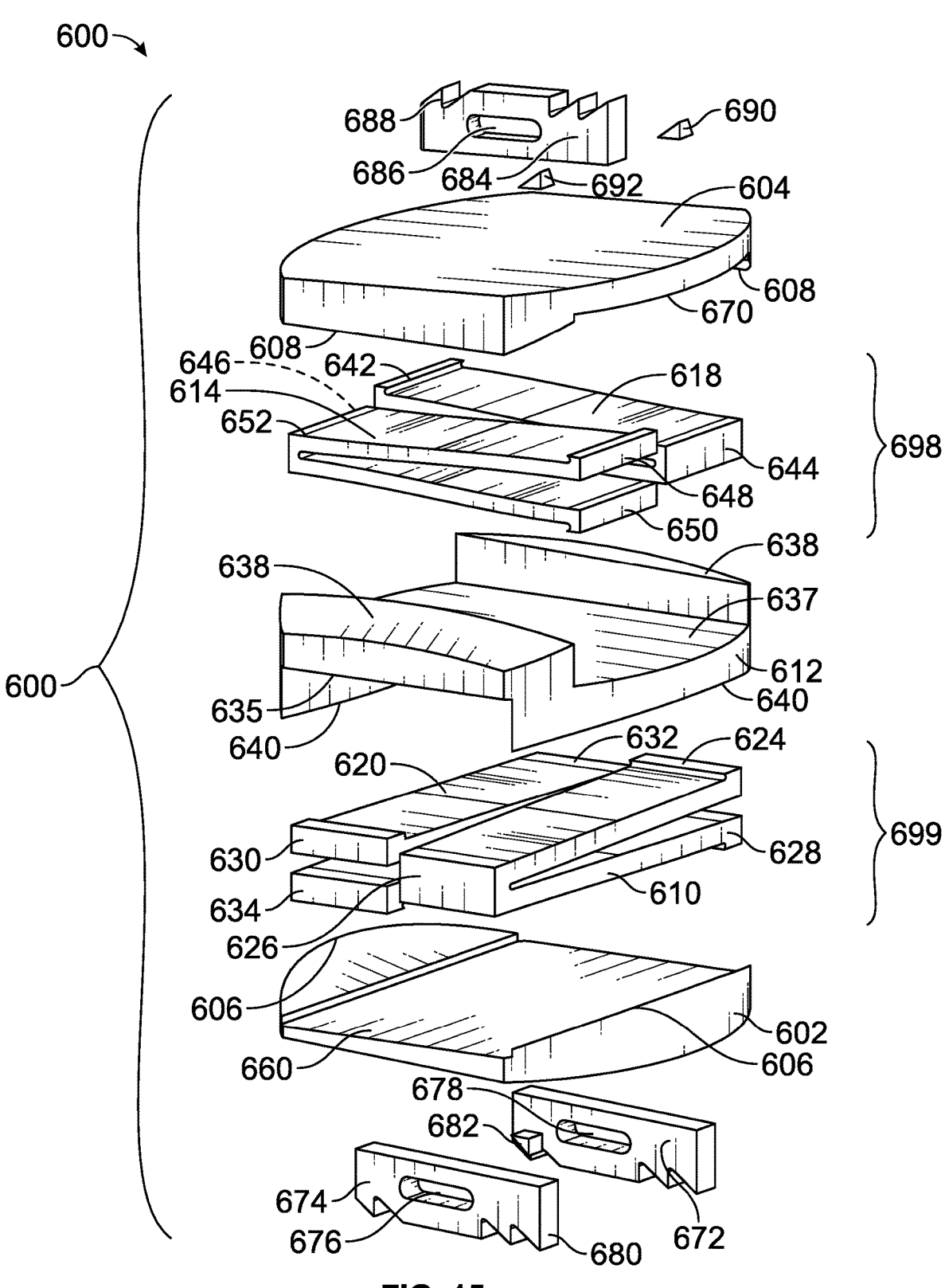
FIG. 15. is an exploded view of the anteriorly inserted compliant device of FIG. 13, according to another embodiment.

Turning to FIG. 15, one embodiment of a compliant device 600 is provided. The compliant device 600 includes a first rigid component 602, a second rigid component 604, a third rigid component 612, a first flexible component 610, a second flexible component 620, a third flexible component 614, and a fourth flexible component 618. In multiple embodiments, the compliant device 600 may have at least one or two degrees of rotational freedom. In some embodiments, the compliant device 600 may include initial spacing in between the interacting rigid components 602, 604, 612.

In various embodiments, the compliant device 600 can optionally include fixation structures. In some embodiments, the fixation structure may be keels or spikes or any other suitable structure to hold the implant in place. In some embodiments, the device includes at least one keel. In alternative embodiments, the device includes at least one keel with a hole. In various embodiments, the at least one keel can be shaped in any shape. In various embodiments, the at least one keel can be shaped in a jagged or spiked shape. In at least one embodiment, the portion of the keels where the keel would contact bone can have a jagged or spikey shaped region 688. In some embodiments, there are at least 1, at least 2, or at least 3 jagged peaks on the surface of the keel that would contact bone.

In some embodiments the compliant device 600 can include a first keel 672, a second keel 674, and a third keel 684. In additional embodiments, the first keel 672 may include a first hole 678. In another embodiment, the second keel 674 includes a second hole 676. In a further embodiment, the third keel 684 can include a third hole 686. Additionally, the compliant device 600 may include at least one or at least two friction structures. In some embodiments, the friction structures may be any shape. In other embodiments, the friction structures may be triangle, cone shaped, spike shaped, or any other suitable shape. Some embodiments of the compliant device 600 may include a first friction structure 690, a second friction structure 692, and a third friction structure 682.

In one embodiment, the compliant device 600 can include at least the first rigid component 602, the second rigid component 604, and/or the third rigid component 612 designed to include at least one rounded bearing surface. In various embodiments, the first rigid component can be designed in any shape. In another embodiment, the first rigid component 602 may include at least one or two rounded bearing surfaces 606 on opposite sides of the first rigid component 602 for contact with the third rigid component 612.

In various embodiments, the second rigid component 604 can be designed in any shape. In another embodiment, the second rigid component 604 may include at least one or two bearing surfaces 608 on opposite sides of the second rigid component 604 for contact with the third rigid component 612. The second rigid component 604 can also include a lower contact surface 670 for interacting with the third and fourth flexible components 614, 618.

In multiple embodiments, the third rigid component 612 can be designed in any shape. In another embodiment, the third rigid component 612 may include at least one lower bearing surface 640 for contact with the first rigid component 602. In additional embodiments, the third rigid component 612 may include at least one or two upper rounded bearing surfaces 638 on opposite sides of the third rigid component 612 for contact with the second rigid component 604. In some embodiments, the third component 612 may also include an upper surface 637 that contacts the third and fourth flexible components 614, 618. In some embodiments, the first component 602 may also include an upper surface 660 that contacts the first and second flexible components 610, 620.

Figure 16:
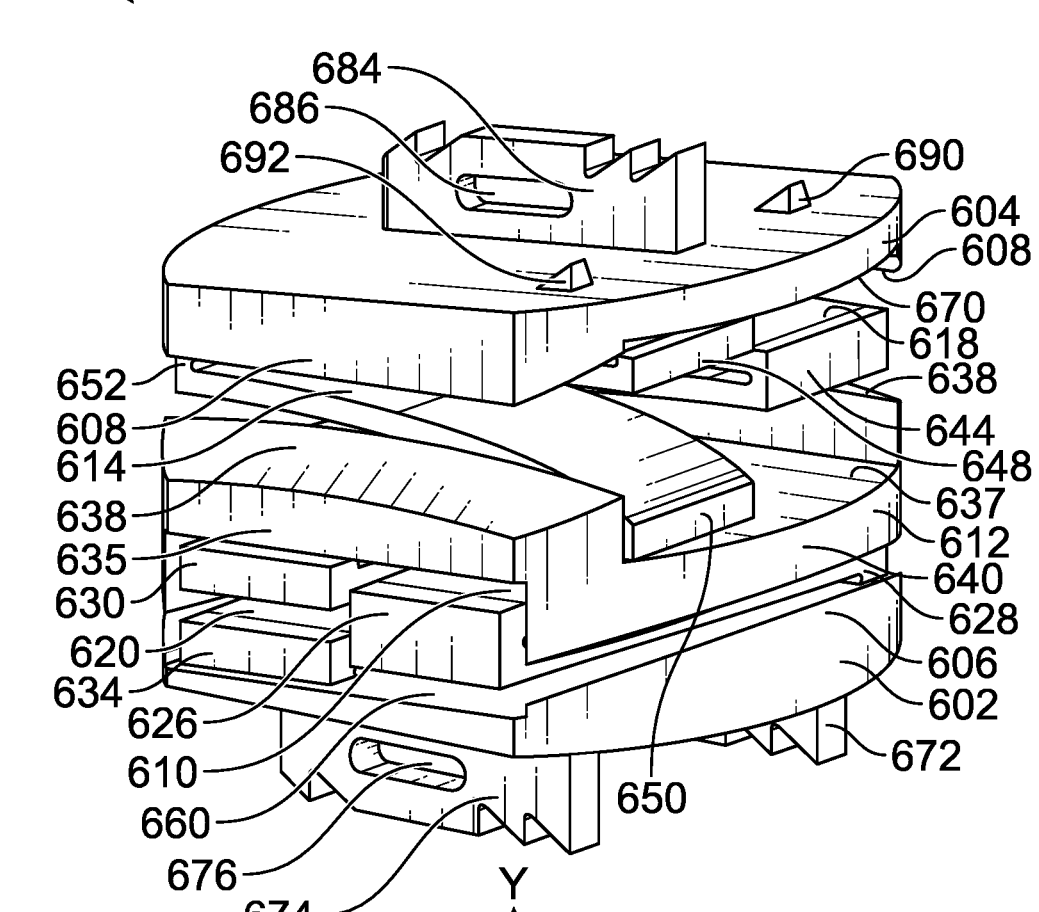
FIG. 16 is a perspective view of the anteriorly inserted compliant device of FIG. 13 in a neutral position, according to one embodiment.
Figure 17:
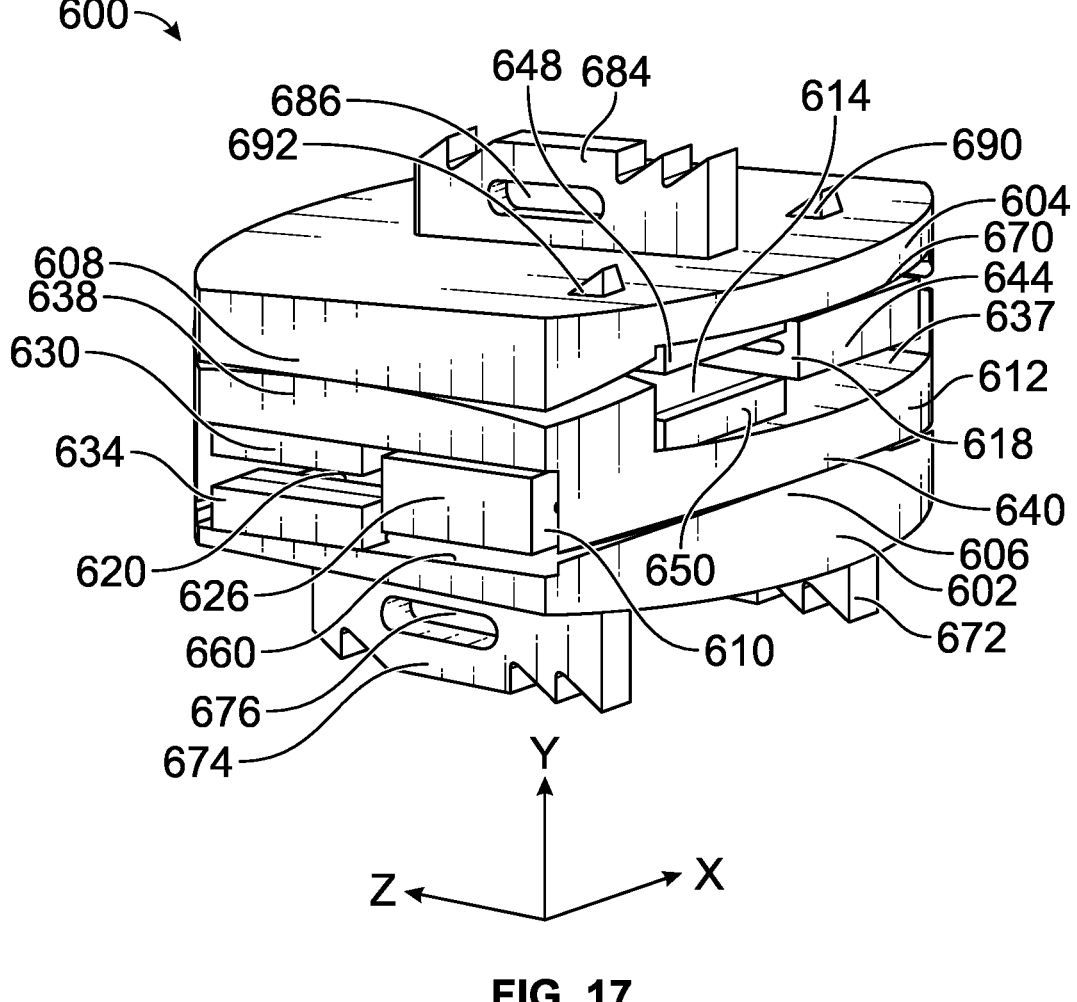
FIG. 17 is a perspective view of the anteriorly inserted compliant device of FIG. 13 in a vertically compressed position, according to one embodiment.
Figure 18:
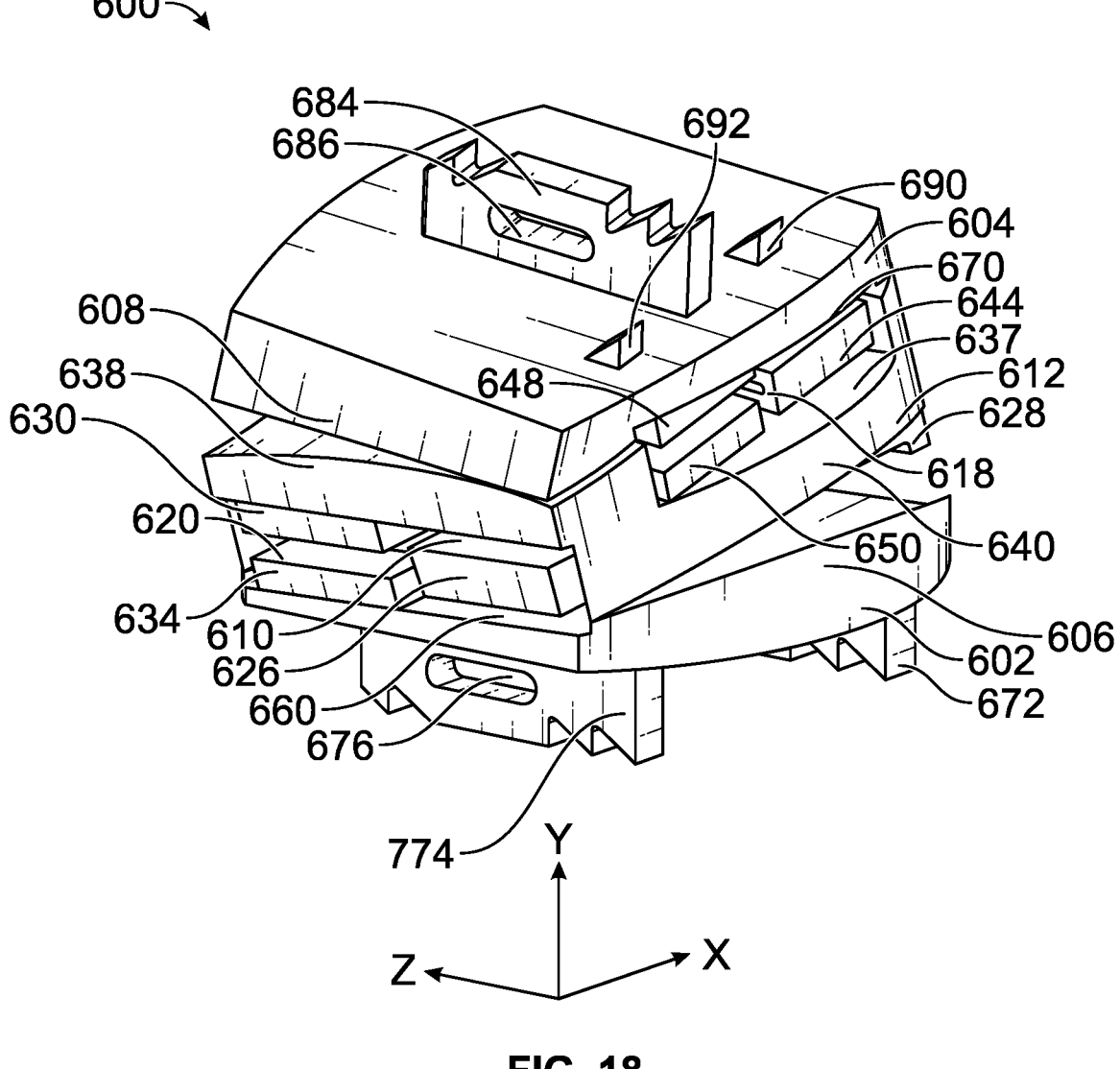
FIG. 18 is a perspective view of the anteriorly inserted compliant device of FIG. 13 in a vertically compressed and rotated position, according to one embodiment.

In multiple embodiments of the compliant device 600 the first rigid component 602 may be a lowermost rigid body with at least one or two bearing surfaces 606 which can control the rotation about the x axis (See FIGS. 16-18). In various embodiments of the device, the first and second flexible components 610, 620 can allow for rotation about the x axis (See FIGS. 16-18). In multiple embodiments of the compliant device 600 the third rigid component 612 may be a middle rigid body comprising at least one lower rounded bearing surface 640 which can control the x axis rotation and at least one or two upper rounded bearing surfaces 638 of the third rigid component 612 which can control the z axis rotation (See FIGS. 16-18). In some embodiments, the third and fourth flexible components 614, 618 can allow for rotation about the z axis (See FIGS. 16-18). In additional embodiments, the second rigid component 604 may be an uppermost rigid body with at least one or two bearing surfaces 608 which can control rotation about the z axis (See FIGS. 16-18).

In some embodiments of device 600, the first flexible component 610 can include a first end 624, a second end 626, and a third end 628, wherein the first flexible component 610 is V-shaped and the second end 626 is the vertex. In various embodiments of device 600, the second flexible component 620 can include a first end 630, a second end 632, and a third end 634, wherein the second flexible component 620 is V-shaped and the second end 632 is the vertex. In multiple embodiments, the third flexible component 614 can include a first end 648, a second end 652, and a third end 650, wherein the third flexible component 614 is V-shaped and the second end 652 is the vertex. In yet another embodiment, the fourth flexible component 618 can include a first end 642, a second end 644, and a third end 646, wherein the fourth flexible component 618 is V-shaped and the second end 644 is the vertex. In various embodiments of the compliant device 600, one or more of the first ends 624, 630, 648, 642 and third ends 628, 634, 650, 646 of the flexible components can include a ledge or tab structure. In some embodiments, the ledge or tab structure may be oriented facing outward. In alternative embodiments, the ledge or tab structure may be oriented facing inward.

As shown in FIG. 15, in multiple embodiments of the compliant device 600 the first and second flexible components 610, 620 can be positioned in an INV-CORE configuration wherein the first and second flexible components 610, 620 can be positioned in parallel with each other wherein the second ends 626, 632 are positioned opposite sides of the compliant device 600 and the first and third ends 624, 628, 630, 634 are positioned on opposite sides of the compliant device 600. In additional embodiments, the third and fourth flexible components 614, 618 can also be oriented in an INV-CORE configuration. In various embodiments, the INV-CORE configuration can include a structure with multiple traversal flexible components. In some embodiments, the third and fourth flexible components 614, 618 are in an INV-CORE configuration and oriented at about a 90-degree angle compared to the first and second flexible components 610, 620 which are also in an INV-CORE configuration.

In various embodiments, the INV-CORE configuration can include rolling features to the lateral edges with the flexible components 610, 620, 614, 618 placed in the central body of the mechanism. In some embodiments, the advantages of the INV-CORE configuration in the compliant device 600 over other mechanisms and/or configuration can include tailorable curvature of the rolling contact surface, mechanical stiffness determined by the mechanical properties of the material and the dimensions of the connecting flexural elements), which can avoid pinching the flexures themselves between the rolling contact surfaces. Additionally in some embodiments of device 600, the INV-CORE configuration can allow the flexible components to be used as compliant springs which can support loading of the surface prior to contact between the rolling contact surfaces, which can yield capability for the INV-CORE configuration to provide tailored force-displacement stiffness response along the axes.

In alternative embodiments of the compliant device 600 the first and second flexible components 610, 620 can be positioned in an INT-CORE configuration wherein the first and second flexible components 610, 620 can be positioned in line with each other wherein the second ends 626, 632 are positioned adjacent to each other and the first and third ends 624, 628, 630, 634 are positioned at opposite sides of the compliant device 600. In various embodiments, the INT-CORE configuration can include a structure with multiple half-traversal flexible components.

In yet another alternative embodiment, flexible components 610, 620 and/or 614, 618 can be positioned wherein the second ends 626, 632, 644, 652, are at the same side of the compliant device 600 and the first ends 624, 630, 642, 648 and third ends 628, 634, 646, 650 are at the other side of the device.

In other embodiments, the compliant device 600 can include an upper portion 698 and a lower portion 699. In various embodiments and as shown in FIG. 15, the compliant device 600 can include the upper portion 698 of at least two flexible components 614, 618 configured in an INV-CORE configuration and the lower portion 699 of at least two flexible components 610, 620 configured in an INV-CORE configuration. In some embodiments, the flexible components 614, 618 of the upper portion 698 may control the rotation about the Z-axis and the flexible components 610, 620 of the lower portion 699 may control the rotation about the X-axis. In multiple embodiments, both the upper portion 698 and the lower portion 699 may include at least two sets of flexible components to connect the rigid components and provide expansion in the y direction.

In multiple embodiments, the compliant device 600 can be designed where the flexible components in both the upper portion 698 and the lower portion 699 are configured in an INV-CORE configuration. In other embodiments, the compliant device 600 can comprise the flexible components of the upper portion 698 configured in an INT-CORE configuration and the flexible components of the lower portion 699 configured in an INV-CORE configuration. In another alternative embodiment, the compliant device 600 can comprise the flexible components of the upper portion 698 configured in an INV-CORE configuration and the flexible components of the lower portion 699 configured in an INT-CORE configuration. In yet another alternative embodiment, the compliant device 600 can be designed where the flexible components in both the upper portion 698 and the lower portion 699 are configured in an INT-CORE configuration.

In multiple embodiments, the compliant device 600 can be used as a minimally invasive spinal disc. In some embodiments, the compliant device 600 is comprised of two or more INV-CORE and/or INT-CORE configurations stacked with a 90-degree rotation relative to each other.

In many embodiments, a compliant device 600 with a configuration of at least 2 stacked INV-CORE configurations can be used in an implant which can provide advantages to the implant. In many embodiments wherein the device contains a stacked INV-CORE and/or a stacked INT-CORE configuration, the combined configuration yields an optimized combination of mechanical support and flexibility.

Referring now to FIGS. 16-18, one embodiment of the compliant device 600 in various positions is provided. FIGS. 16-18 show the actuation of the compliant device 600 from completely neutral, to compressed vertically, to compressed and rotated. In some embodiments, rotation can occur without compression. In some embodiments, when the compliant device 600 is compressed, the curvature of the contact surfaces can control the rotation pathway and changes in the orientation and location of the instantaneous screw axis. In additional embodiments, when the compliant device 600 is not fully compressed, the stiffness and orientation of the flexures controls the orientation and axis of the instantaneous screw axis.

As shown in FIG. 16, in some embodiments, the compliant device 600 can hold a neutral position wherein there is a maximal amount of space between the rigid components 602, 604, 612. In some embodiments, the compliant device 600 can be designed so that in the neutral position, the first and second rigid components 602, 604 are parallel. In additional embodiments, the flexible components can be manufactured wherein the neutral position of the first and second rigid components 602, 604 could be angled in any number of ways. In various embodiments, the compliant device 600 as used in a spinal implant may include a default rotation about the X-axis as it is determined, to allow for a natural lordotic curvature of the spine.

As shown in FIG. 17, in multiple embodiments, the compliant device 600 can also be vertically compressed along a y axis wherein the amount of space between the rigid components 602, 604, 612 is compressed along the y axis and the rigid components 602, 604, 612 make contact with one another via the contact points. In various embodiments, the flexible components 610, 620, 614, 618 can compress and allow for rolling contact to control the motion and/or rotation of the compliant device 600.

In another embodiment of the compliant device 600, upon vertical compression the at least one or two bearing surfaces 606 of the first rigid component 602 on opposite sides of the first rigid component 602 can make contact with the third rigid component 612 at the at least one lower bearing surface 640 of the third rigid component 612. In some embodiments of the compliant device 600, upon vertical compression the at least two edges with a bearing surface 608 of the second rigid component 604 on opposite sides of the second rigid component 604 can make contact with the third rigid component 612 at the at least one upper rounded bearing surface 638 of the third rigid component 612.

As shown in FIG. 18, in some embodiments, the compliant device 600 can also be compressed along a y axis as well as rotated along the z and or x axis. As described in FIG. 15, in multiple embodiments of the compliant device 600 the first rigid component 602 may be a lowermost rigid body with at least one or two bearing surfaces 606 which can control the rotation about the x axis. In various embodiments of the device, the first and second flexible components 610, 620 can allow for rotation about the x axis. In multiple embodiments of the compliant device 600 the third rigid component 612 may be a middle rigid body comprising at least one lower bearing surface 640 which can control the x axis rotation and at least one or two upper rounded bearing surfaces 638 of the third rigid component 612 which can control the z axis rotation. In some embodiments, the third and fourth flexible components 614, 618 can allow for rotation about the z axis. In additional embodiments, the second rigid component 604 may be an uppermost rigid body with at least one or two rounded bearing surfaces 608 which can control rotation about the z axis. In various embodiments, the motion of the compliant device 600 can be tightly controlled by designing the compliant device 600 using features that would stop the device from rotating beyond a certain point.

In various embodiments, at least two of the compliant device 600 can be inserted bilaterally in a similar surgical approach to the surgical approach for a minimally invasive posterior lumbar fusion procedure. In alternative embodiments, the compliant device 600 can be inserted unilaterally.

In some embodiments, because the compliant device 600 is not static, insertion of the compliant device 600 can be done using a minimally invasive total lumbar disc replacement rather than a fusion. In some embodiments, at least one of the compliant device 600 can be inserted alone. In alternative embodiments, the at least one of the compliant device 600 can be implanted in tandem with any outer cage since the compliant device 600 can be size-constrained by surgical window size. In various embodiments, the outer cage can be any cage that can be implanted into the intervertebral space and expand both laterally and vertically. In some embodiments, the outer cage is an expanding outer cage. In various embodiments the expanding outer cage can be a triaxial expanding interbody device. In alternative embodiments, the outer cage is the outer piece of a posterior inter body fusion system, such as the Flare Hawk spinal fusion device by Integrity Implants.

In various embodiments, at least one of the compliant device 600 may be inserted with an outer expandable cage which can provide the benefit of added expandability and the disc replacement can potentially be revised to a fusion procedure with minimal hardware removal. In some embodiments of device 600 insertion, this can be achieved if the outer expanding piece is fixed to the vertebrae, while the inner actuating piece is made to be removable and can be replaced with a static insert (e.g., revision to a fusion), or with a replacement spinal disc device with equal or different mechanical properties (e.g., an identical device).

In some embodiments, the compliant device 600 can be designed to be any interbody device. In some embodiments, the compliant device 600 can be manufactured using additive manufacturing. In a particular embodiment, the additive manufacturing can be 3D printing. In some embodiments, the compliant device 600 can be manufactured as a single piece using additive manufacturing. In additional embodiments, the device 600 can be designed in a patient specific manner.

Figure 19:
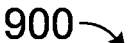
FIG. 19 is a left lateral view of a spine with one laterally inserted compliant device placed within for lumbar disc replacement, according to one embodiment.
Figure 19:
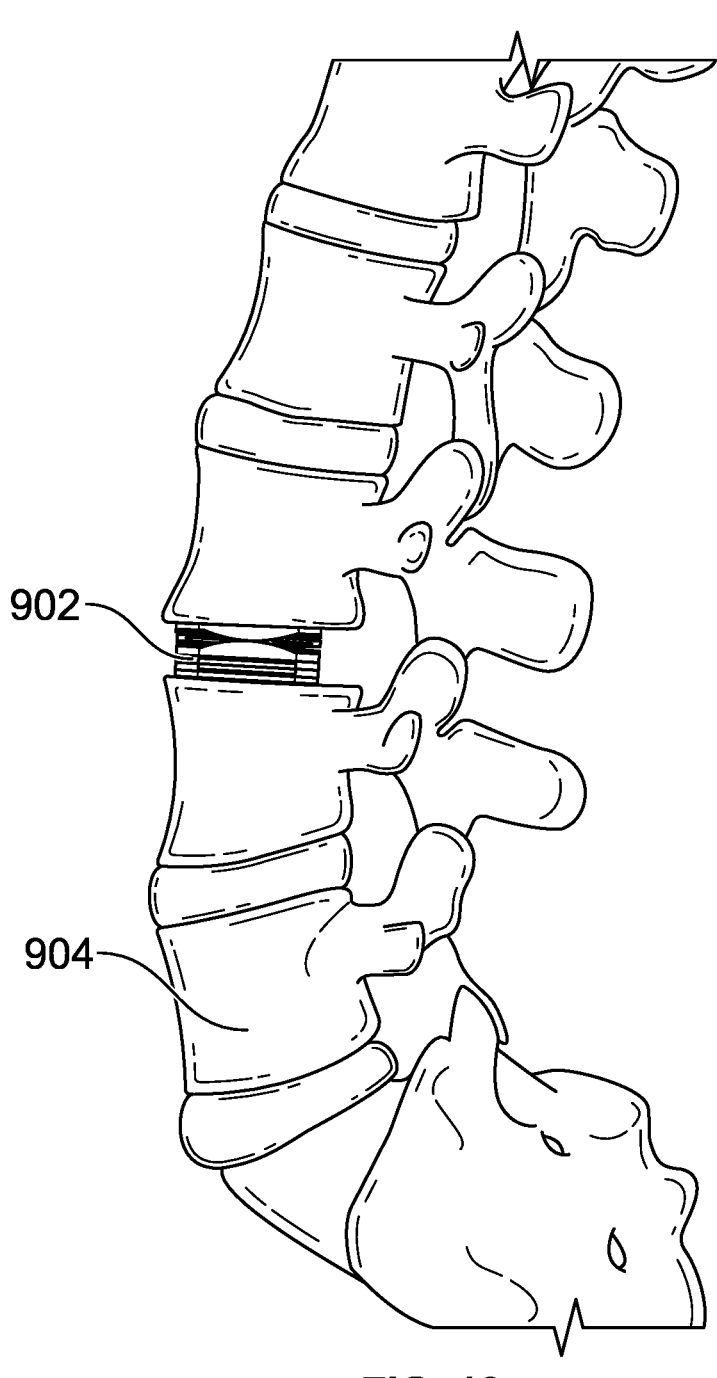
Figure 20:
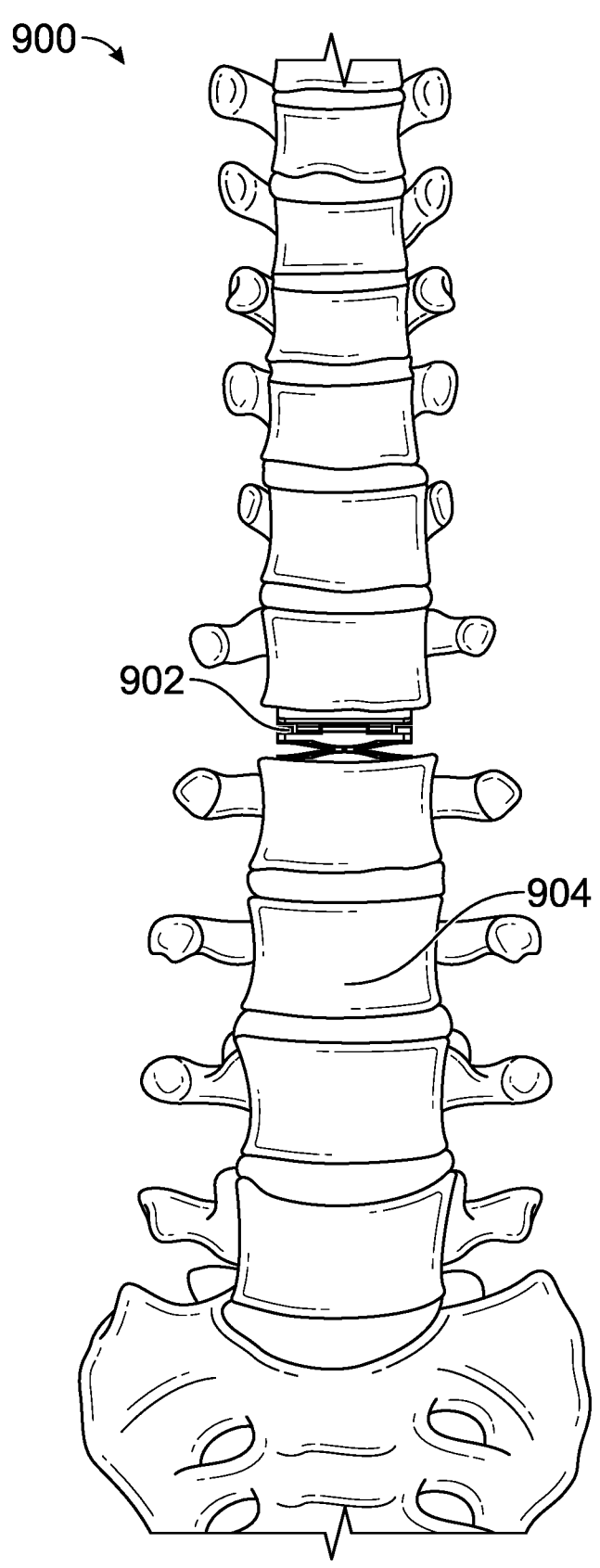
FIG. 20 is an anterior view of a spine with one laterally inserted compliant device placed within for lumbar disc replacement, according to one embodiment.
Figure 21:
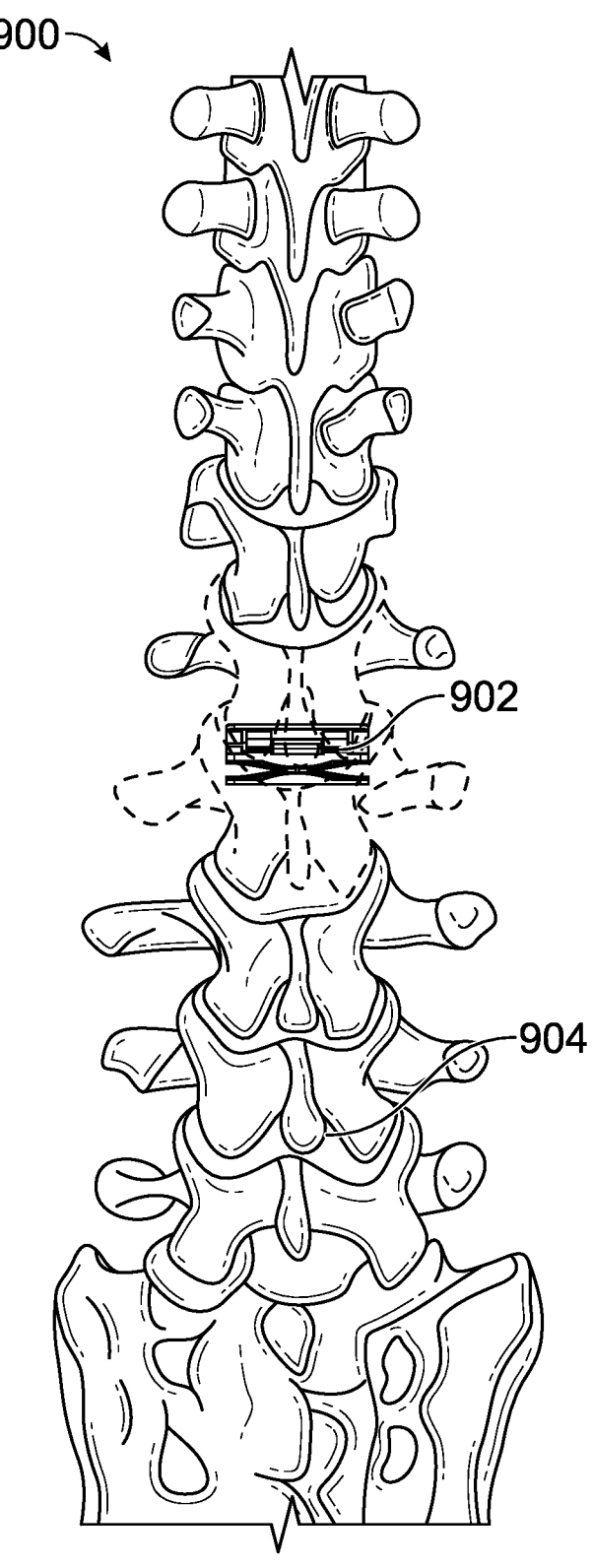
FIG. 21 is a posterior view of a spine with one laterally inserted compliant device placed within for lumbar disc replacement, according to one embodiment.

Turning now to FIGS. 19-21, a compliant device 900 inserted into a spine 904 is shown. In various embodiments, the compliant device 900 includes an implant body 902. In at least one embodiment, the compliant device 900 can be inserted into the spine 904. In alternative embodiments, the compliant device 900 can be inserted into a knee, ankle, wrist, elbow, or any other suitable joint or anatomic structure of a human or other animal.

In some embodiments wherein the compliant device 900 can be inserted into the spine 904, the compliant device 900 can be inserted laterally. In additional embodiments, the compliant device 900 can be inserted into a lumbar region of the spine 904. In various embodiments, the compliant device 900 can be used as a minimally invasive device for total lumbar disc replacement. In some embodiments, the compliant device 900 can be used unilaterally. In alternative embodiments, the compliant device 900 can be used bilaterally. In embodiments when used bilaterally, the compliant device 900 can provide appropriate restorative forces and moments to the spinal segment, which can enable restoration of both the quantity of mechanical motion (e.g., range of motion), as well as the quality of motion (e.g., rotational and translational stiffness).

In some embodiments, the compliant device 900 can be designed to be any interbody device. In some embodiments, the compliant device 900 can be manufactured using additive manufacturing. In a particular embodiment, the additive manufacturing can be 3D printing. In some embodiments, the compliant device 900 can be manufactured as a single piece using additive manufacturing. In additional embodiments, the device 900 can be designed in a patient specific manner.

Figure 22:
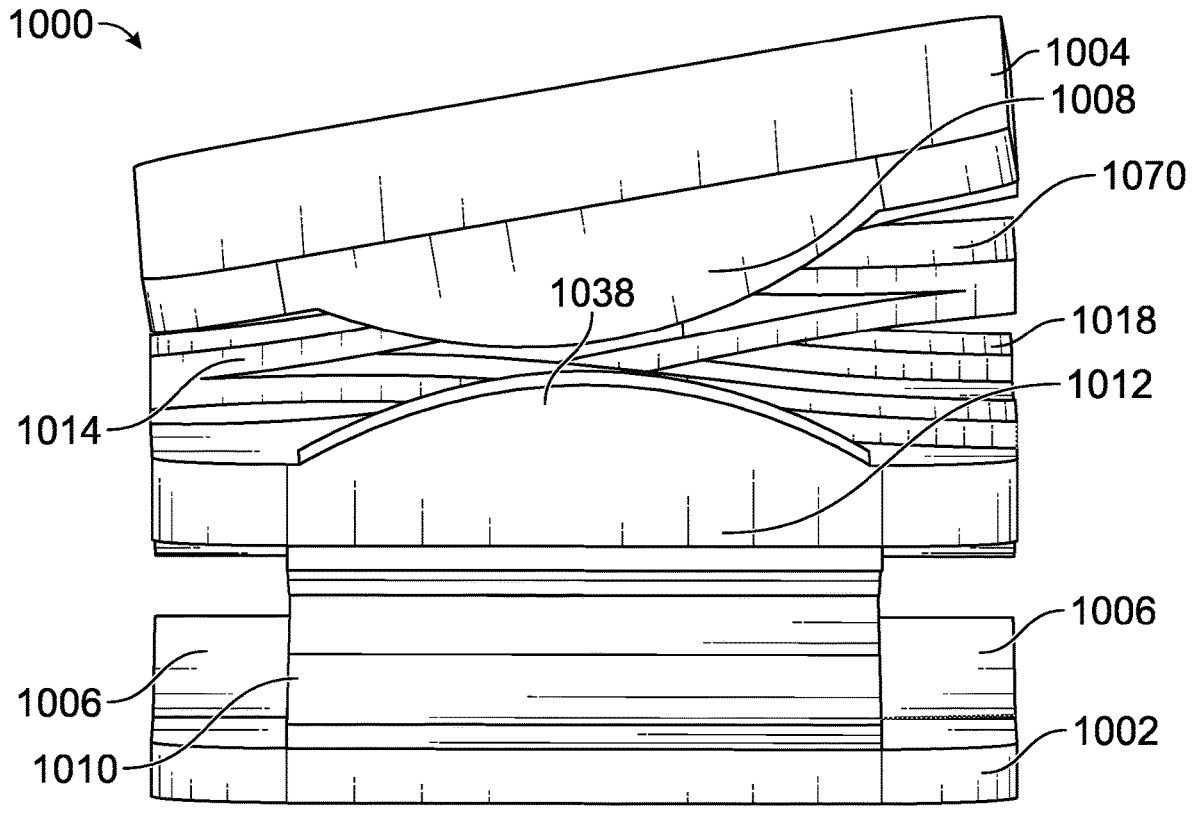
FIG. 22 is a side view of one laterally inserted compliant device, according to another embodiment.
Figure 23:
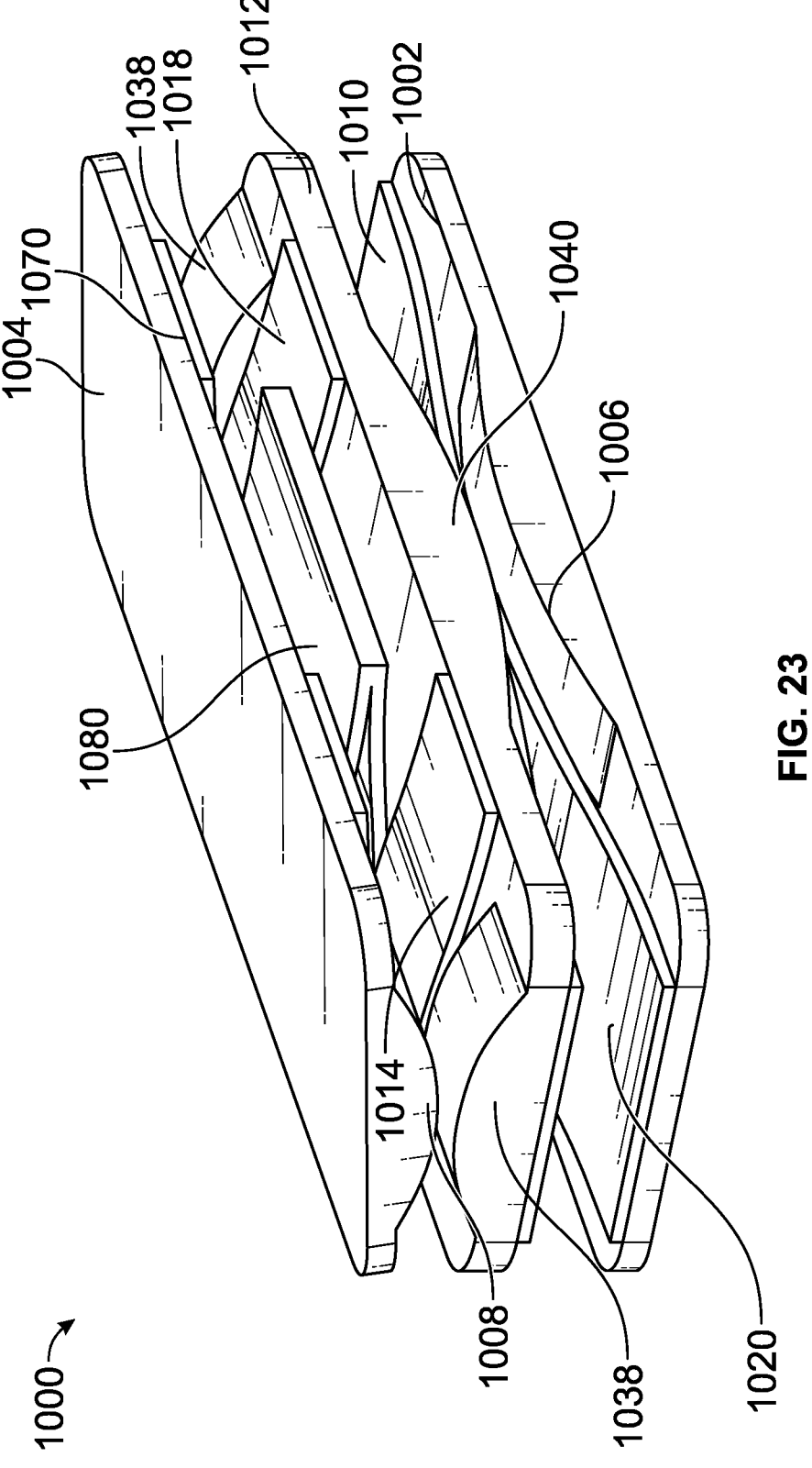
FIG. 23 is a perspective view of the laterally inserted compliant device of FIG. 22.

Referring now to FIGS. 22-23, one embodiment of a compliant device 1000 is provided. The compliant device 1000 includes a first rigid component 1002, a second rigid component 1004, a third rigid component 1012, a first flexible component 1010, a second flexible component 1020, a third flexible component 1014, a fourth flexible component 1018, and a fifth flexible component 1080. In multiple embodiments, the compliant device 1000 may have at least one or two degrees of rotational freedom. In some embodiments, the compliant device 1000 may include initial spacing in between the interacting rigid components 1002, 1004, 1012. In various embodiments, the compliant device 1000 is designed using inverted contact-aided rolling element (ICORE) mechanisms. In various embodiments, the compliant device 1000 is used as a spinal implant. In an additional embodiment, the compliant device 1000 is laterally inserted for total lumbar spinal disc replacement.

In one embodiment, the compliant device 1000 can include at least the first rigid component 1002, the second rigid component 1004, and/or the third rigid component 1012 designed to include at least one rounded bearing surface. In various embodiments, the first rigid component 1002 can be designed in any shape. In another embodiment, the first rigid component 1002 may include at least one or two rounded bearing surfaces 1006 on opposite sides of the first rigid component 1002 for contact with the third rigid component 1012.

In various embodiments, the second rigid component 1004 can be designed in any shape. In another embodiment, the second rigid component 1004 may include at least one or two rounded bearing surfaces 1008 on opposite sides of the second rigid component 1004 for contact with the third rigid component 1012.

In multiple embodiments, the third rigid component 1012 can be designed in any shape. In another embodiment, the third rigid component 1012 may include at least one or two lower rounded bearing surfaces 1040 for contact with the first rigid component 1002. In additional embodiments, the third rigid component 1012 may include at least one or two upper rounded bearing surfaces 1038 on opposite sides of the third rigid component 1012 for contact with the second rigid component 1004.

In some embodiments, the flexible components 1010, 1020, 1014, 1018, 1080 can be designed in any shape. In various embodiments, the flexible components 1010, 1020, 1014, 1018, 1080 can be designed in a V-shape having two regions extending from a vertex. In some embodiments, the shape of the two regions extending from the vertex can have a curvature with a radius of curvature of at least 20 mm, at least 30 mm, at least 60 mm, at least 70 mm. In alternative embodiments, the shape of the two regions extending from the vertex can have can be substantially straight.

In various embodiments, the flexible components 1010, 1020, 1014, 1018, 1080 may be configured having a Euler spiral. In yet other embodiments, the shape of the two regions extending from the vertex may be a deployable Euler spiral connector (DESC), which provides maximum compressibility for packing purposes. See U.S. Patent Publication 2022/0047397 incorporated by reference in its entirety.

In various embodiments, the flexible components 1010, 1020, 1014, 1018, 1080 can have a thickness of at least 0.5 mm, 1 mm, 1.5 mm, 2 mm, or 5 mm. In various embodiments, the first flexible component 210 has a width of at least 5 mm, at least 7 mm, at least 14 mm, at least 20 mm. In various embodiments of device 1000, the width of the fifth flexible component 1080 can be greater than the width of the third and fourth flexible components 1014, 1018.

In various embodiments, the compliant device 1000 can be inserted into a spine. In additional embodiments, the compliant device 1000 can be used unilaterally or bilaterally. In some embodiments, the compliant device 1000 can be inserted posteriorly into the spine. In various embodiments, when used bilaterally, the vertical flex of the compliant device 1000 can provide appropriate restorative forces and moments to the spinal segment, which can enable restoration of both the quantity of mechanical motion (e.g., range of motion), as well as the quality of motion (e.g., rotational and translational stiffness).

Figure 24:
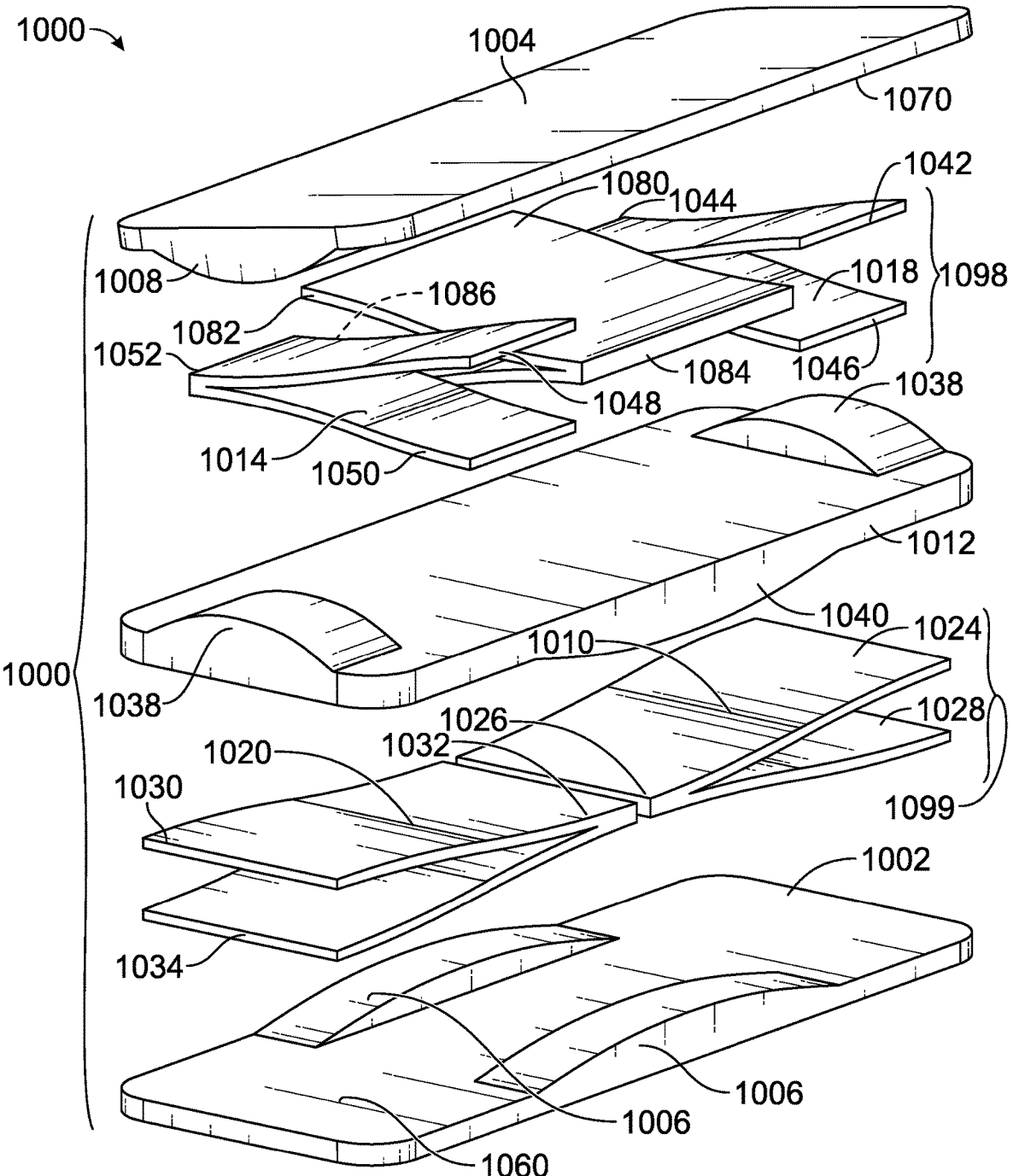
FIG. 24 is an exploded view of the laterally inserted compliant device of FIG. 22, according to another embodiment.

Turning to FIG. 24, one embodiment of a compliant device 1000 is provided. The compliant device 1000 includes a first rigid component 1002, a second rigid component 1004, a third rigid component 1012, a first flexible component 1010, a second flexible component 1020, a third flexible component 1014, a fourth flexible component 1018, and a fifth flexible component 1080. In multiple embodiments, the compliant device 1000 may have at least one or two degrees of rotational freedom. In some embodiments, the compliant device 1000 may include initial spacing in between the interacting rigid components 1002, 1004, 1012.

In one embodiment, the compliant device 1000 can include at least the first rigid component 1002, the second rigid component 1004, and/or the third rigid component 1012 designed to include at least one rounded bearing surface. In various embodiments, the first rigid component 1002 can be designed in any shape. In another embodiment, the first rigid component 1002 may include at least one or two rounded bearing surfaces 1006 on opposite sides of the first rigid component 1002 for contact with the third rigid component 1012.

In various embodiments, the second rigid component 1004 can be designed in any shape. In another embodiment, the second rigid component 1004 may include at least one or two rounded bearing surfaces 1008 on opposite sides of the second rigid component 1004 for contact with the third rigid component 1012.

In multiple embodiments, the third rigid component 1012 can be designed in any shape. In another embodiment, the third rigid component 1012 may include at least one lower rounded bearing surface 1040 for contact with the first rigid component 1002. In additional embodiments, the third rigid component 1012 may include at least one or two upper rounded bearing surfaces 1038 on opposite sides of the third rigid component 1012 for contact with the second rigid component 1004.

Figure 25:
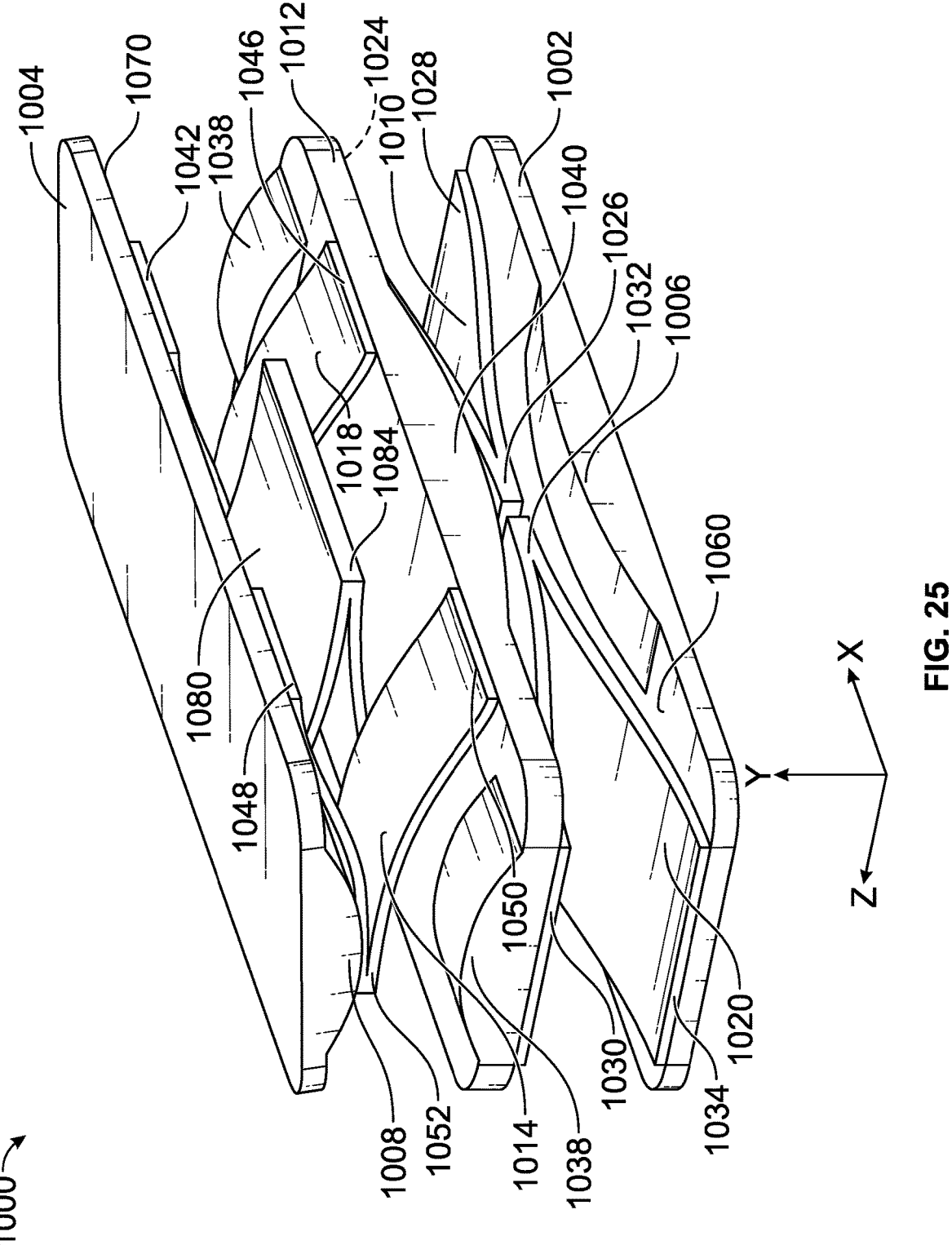
FIG. 25 is a perspective view of the laterally inserted compliant device of FIG. 22 in a neutral position, according to one embodiment.
Figure 26:
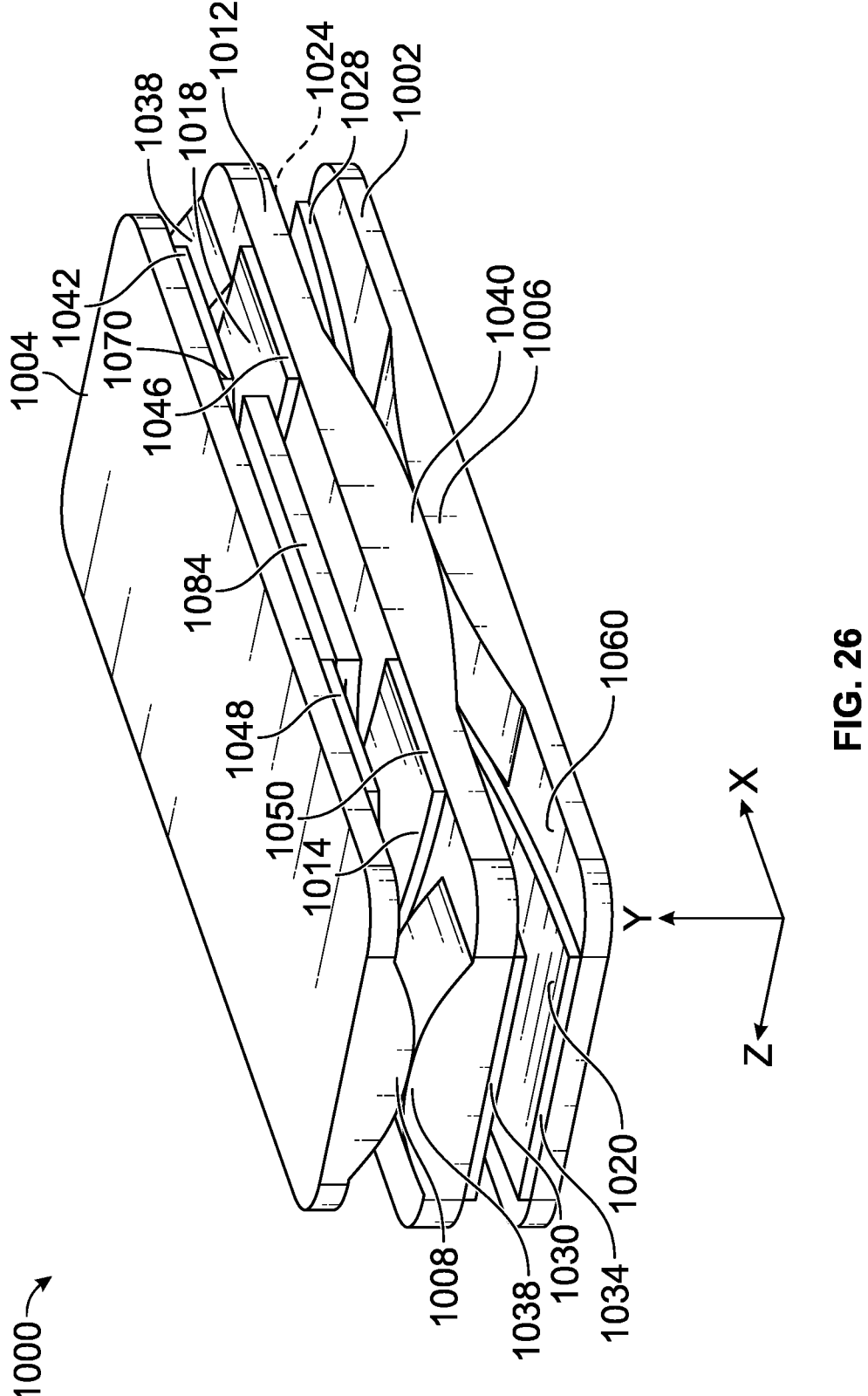
FIG. 26 is a perspective view of the laterally inserted compliant device of FIG. 22 in a vertically compressed position, according to one embodiment.
Figure 27:
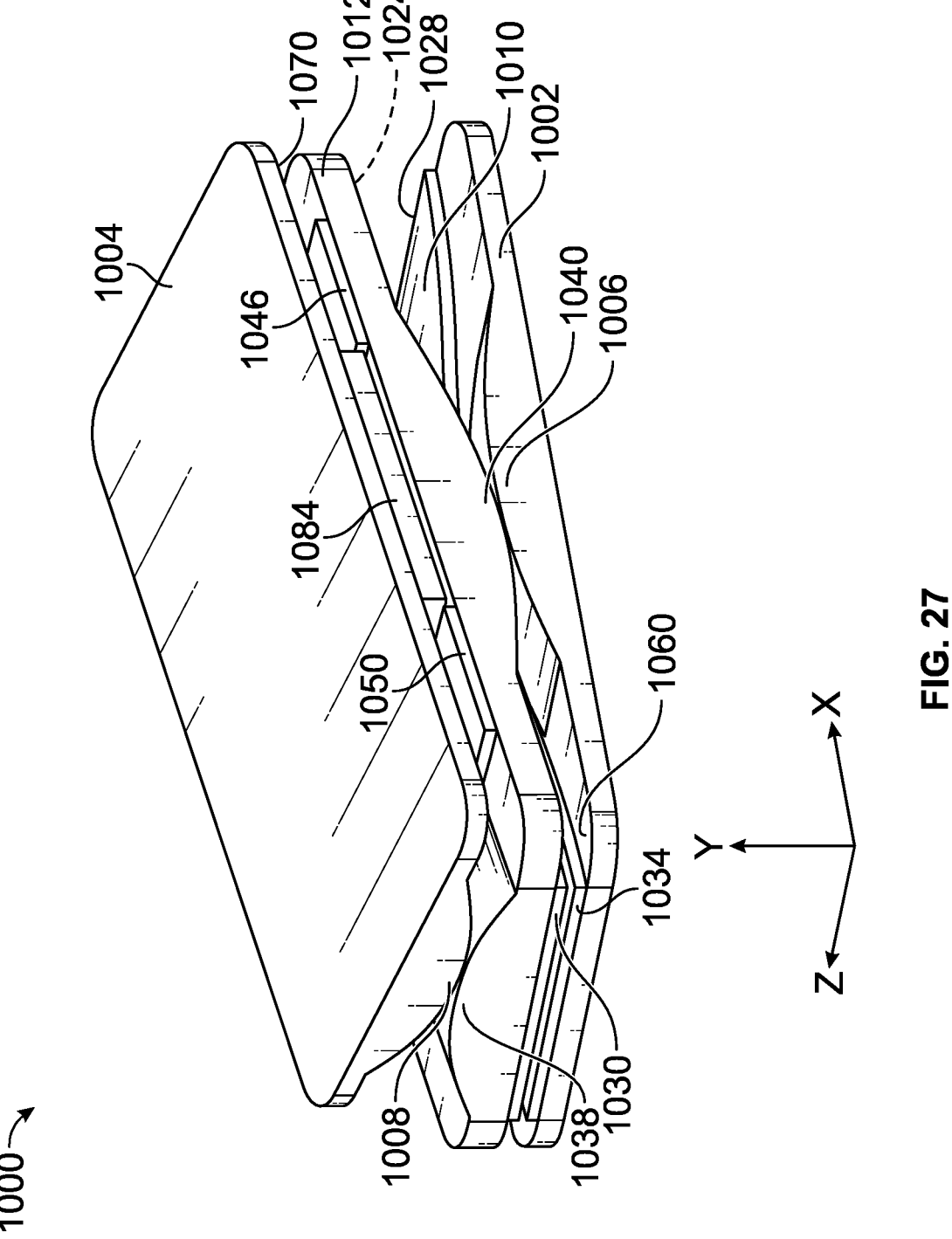
FIG. 27 is a perspective view of the laterally inserted compliant device of FIG. 22 in a vertically compressed and rotated position, according to one embodiment.

In multiple embodiments of the compliant device 1000 the first rigid component 1002 may be a lowermost rigid body with at least one or two rounded bearing surfaces 1006 which can control the rotation about the x axis (See FIGS. 25-27). In various embodiments of the device, the first and second flexible components 1010, 1020 can allow for rotation about the x axis. In multiple embodiments of the compliant device 1000 the third rigid component 1012 may be a middle rigid body comprising at least one lower rounded bearing surface 1040 which can control the x axis rotation and at least one or two upper rounded bearing surfaces 1038 of the third rigid component 1012 which can control the z axis rotation (See FIGS. 25-27). In some embodiments, the third, fourth, and fifth flexible components 1014, 1018, 1080 can allow for rotation about the z axis (See FIGS. 25-27). In additional embodiments, the second rigid component 1004 may be an uppermost rigid body with at least one or two rounded bearing surfaces 1008 which can control rotation about the z axis (See FIGS. 25-27).

In some embodiments of device 1000, the first flexible component 1010 can include a first end 1024, a second end 1026, and a third end 1028, wherein the first flexible component 1010 is V-shaped and the second end 1026 is the vertex. In various embodiments of device 1000, the second flexible component 1020 can include a first end 1030, a second end 1032, and a third end 1034, wherein the second flexible component 1020 is V-shaped and the second end 1032 is the vertex. In multiple embodiments, the third flexible component 1014 can include a first end 1048, a second end 1052, and a third end 1050, wherein the third flexible component 1014 is V-shaped and the second end 1052 is the vertex. In yet another embodiment, the fourth flexible component 1018 can include a first end 1042, a second end 1044, and a third end 1046, wherein the fourth flexible component 1018 is V-shaped and the second end 1044 is the vertex.

In another embodiment, the fifth flexible component 1080 can include a first end 1082, a second end 1084, and a third end 1086, wherein the fifth flexible component 1080 is V-shaped and the second end 1084 is the vertex.

In additional embodiments, the compliant device 1000 can include at least one surface which can contact the flexible components (e.g., 1010, 1020). In some embodiments, the compliant device 1000 can include a first surface 1060 and a second surface 1065. In some embodiments, the compliant device 1000 includes the first surface 1060 and the second surface 1065 which are flat and can contact the first and second flexible components 1010, 1020.

In various embodiments, and as shown in FIG. 24, of the compliant device 1000 the first and second flexible components 1010, 1020 can be positioned in an INT-CORE configuration wherein the first and second flexible components 1010, 1020 can be positioned in line with each other wherein the second ends 1026, 1032 are positioned adjacent to each other and the first and third ends 1024, 1028, 1030, 1034 are positioned at opposite sides of the compliant device 1000. In various embodiments, the INT-CORE configuration can include a structure with multiple half-traversal flexible components. In various embodiments, the advantages of the INT-CORE configuration over other mechanisms and/or configuration can include improved space utilization, avoidance of pinching of the flexures between the rolling contact surfaces, and increased ease of manufacturing.

In alternative embodiments, the first and second flexible components 1010, 1020 can be oriented in an INV-CORE configuration wherein the first and second flexible components 1010, 1020 can be positioned in parallel with each other wherein the second ends 1026, 1032 are positioned opposite sides of the compliant device 1000 and the first and third ends 1024, 1028, 1030, 1034 are positioned on opposite sides of the compliant device 1000.

In various embodiments and as shown in FIG. 24, the third, fourth, and fifth flexible components 1014, 1018, 1080 of the compliant device 1000 can be oriented in an INV-CORE configuration. In various embodiments, the INV-CORE configuration can include a structure with multiple traversal flexible components.

In various embodiments, the INV-CORE configuration can include rolling features to the lateral edges with the flexible components 1014, 1018, 1080 placed in the central body of the mechanism. In some embodiments, the advantages of the INV-CORE configuration over other mechanisms and/or configuration can include tailorable curvature of the rolling contact surface, mechanical stiffness determined by the mechanical properties of the material and the dimensions of the connecting flexural elements), which can avoid pinching the flexures themselves between the rolling contact surfaces. Additionally in some embodiments, the INV-CORE configuration can allow the flexible components to be used as compliant springs which can support loading of the surface prior to contact between the rolling contact surfaces, which can yield capability for the INV-CORE configuration to provide tailored force-displacement stiffness response along the axes.

In yet another alternative embodiment, flexible components 1010, 1020 and/or 1014, 1018, 1080 can be positioned wherein the second ends 1026, 1032, 1044, 1052, 1084 are at the same side of the compliant device 1000 and the first ends 1024, 1030, 1042, 1048 and third ends 1028, 1034, 1046, 1050, 1082, 1080 are at the other side of the device.

In other embodiments, the compliant device 1000 can include an upper portion 1098 and a lower portion 1099. In various embodiments and as shown in FIG. 24, the compliant device 1000 can include the upper portion 1098 of at least one or more flexible components 1014, 1018, 1080 configured in an INV-CORE configuration and the lower portion 1099 of at least two flexible components 1010, 1020 configured in an INT-CORE configuration. In multiple embodiments, the upper portion 1098 comprises at least one or more flexible components 1014, 1018, 1080 wherein the flexible components are oriented in an alternating pattern. In alternative embodiments, the upper portion 1098 comprises at least one or more flexible components 1014, 1018, 1080 wherein the flexible components are not oriented in an alternating pattern.

In some embodiments, the flexible components 1014, 1018, 1080 of the upper portion 1098 may control the rotation about the Z-axis and the flexible components 1010, 1020 of the lower portion 1099 may control the rotation about the X-axis. In multiple embodiments, both the upper portion 1098 and the lower portion 1099 may include at least two sets of flexible components to connect the rigid components and provide expansion in the y direction.

In various embodiments (and as shown in FIG. 24) the compliant device 1000 can comprise flexible components in the upper portion 1098 configured in an INV-CORE configuration and flexible components in the lower portion 1099 configured in an INT-CORE configuration. In alternative embodiments, the compliant device 1000 can comprise the flexible components of the upper portion 1098 configured in an INT-CORE configuration and the flexible components of the lower portion 1099 configured in an INV-CORE configuration. In yet another alternative embodiment, the compliant device 1000 can be designed where the flexible components in both the upper portion 1098 and the lower portion 1099 are configured in the same configuration (INV-CORE or INT-CORE).

In multiple embodiments, the compliant device 1000 can be used as a minimally invasive spinal disc. In some embodiments, the compliant device 1000 is comprised of two or more INV-CORE and/or INT-CORE configurations stacked with a 90-degree rotation relative to each other.

In other embodiments, the compliant device 1000 is comprised of two or more INV-CORE and/or INT-CORE configurations stacked with any configuration besides a 90-degree rotation relative to each other. In some embodiments, an alternative configuration of the components may allow for the mechanism to avoid movement in a particular region of space, creating a region of avoidance.

In many embodiments, a compliant device 1000 with a configuration of a stacked INV-CORE and/or a stacked INT-CORE configuration can be used in an implant which can provide advantages to the implant. In one embodiment, for a device and/or implant with a non-uniform aspect ratio, the INV-CORE configuration is preferred for the orientation where the rolling bearing surfaces have a rolling path is along the short axis and the INT-CORE configuration is preferred for the orientation where the rolling bearing surfaces have a rolling path along the long-axis. In many embodiments wherein the device contains a stacked INV-CORE and/or a stacked INT-CORE configuration, the combined configuration yields an optimized combination of mechanical support and flexibility.

Referring now to FIGS. 25-27, one embodiment of the compliant device 1000 in various positions is provided. FIGS. 25-27 show the actuation of the compliant device 1000 from completely neutral, to compressed vertically, to compressed and rotated. In some embodiments, rotation can occur without compression. In some embodiments, when the compliant device 1000 is compressed, the curvature of the contact surfaces can control the rotation pathway and changes in the orientation and location of the instantaneous screw axis. In additional embodiments, when the compliant device 1000 is not fully compressed, the stiffness and orientation of the flexures controls the orientation and axis of the instantaneous screw axis.

As shown in FIG. 25, in some embodiments, the compliant device 1000 can hold a neutral position wherein there is a maximal amount of space between the rigid components 1002, 1004, 1012.

In some embodiments, the compliant device 1000 can be designed so that in the neutral position, the first and second rigid components 1002, 1004 are parallel. In additional embodiments, the flexible components can be manufactured wherein the neutral position of the first and second rigid components 1002, 1004 could be angled in any number of ways. In various embodiments, the compliant device 1000 as used in a spinal implant may include a default rotation about the X-axis as it is determined, to allow for a natural lordotic curvature of the spine.

As shown in FIG. 26, in multiple embodiments, the compliant device 1000 can also be vertically compressed along a y axis wherein the amount of space between the rigid components 1002, 1004, 1012 is compressed along the y axis and the rigid components 1002, 1004, 1012 make contact with one another via the rounded contact points. In various embodiments, the flexible components 1010, 1020, 1014, 1018, 1080 can compress and allow for rolling contact to control the motion and/or rotation of the compliant device 1000.

In another embodiment of the compliant device 1000, upon vertical compression the at least one or two rounded bearing surfaces 1006 of the first rigid component 1002 on opposite sides of the first rigid component 1002 can make contact with the third rigid component 1012 at the at least one lower rounded bearing surface 1040 of the third rigid component 1012. In some embodiments of the compliant device 1000, upon vertical compression the at least two edges with a rounded bearing surface 1008 of the second rigid component 1004 on opposite sides of the second rigid component 1004 can make contact with the third rigid component 1012 at the at least one upper edge with an upper rounded bearing surface 1038 of the third rigid component 1012.

As shown in FIG. 27, in some embodiments, the compliant device 1000 can also be compressed along a y axis as well as rotated along the z and or x axis. In various embodiments, the compliant device 1000 can be designed wherein the top and bottom regions of the compliant device 1000 can roll in their respective axes. As described in FIG. 25, in multiple embodiments of the compliant device 1000 the first rigid component 1002 may be a lowermost rigid body with at least one or two rounded bearing surfaces 1006 which can control the rotation about the x axis. In various embodiments of the device, the first and second flexible components 1010, 1020 can allow for rotation about the x axis. In multiple embodiments of the compliant device 1000 the third rigid component 1012 may be a middle rigid body comprising at least one lower rounded bearing surface 1040 which can control the x axis rotation and at least one or two upper rounded bearing surfaces 1038 of the third rigid component 1012 which can control the z axis rotation. In some embodiments, the third, fourth, and fifth flexible components 1014, 1018, 1080 can allow for rotation about the z axis. In additional embodiments, the second rigid component 1004 may be an uppermost rigid body with at least one or two rounded bearing surfaces 1008 which can control rotation about the z axis. In various embodiments, the motion of the compliant device 1000 can be tightly controlled by designing the compliant device 1000 using features that would stop the device from rotating beyond a certain point.

In various embodiments, at least two of the compliant device 1000 can be inserted bilaterally in a similar surgical approach to the surgical approach for a minimally invasive posterior lumbar fusion procedure. In alternative embodiments, the compliant device 1000 can be inserted unilaterally.

In some embodiments, the compliant device 1000 can be designed to be any interbody device. In some embodiments, the compliant device 1000 can be manufactured using additive manufacturing. In a particular embodiment, the additive manufacturing can be 3D printing. In some embodiments, the compliant device 1000 can be manufactured as a single piece using additive manufacturing. In additional embodiments, the device 1000 can be designed in a patient specific manner.

In some embodiments, because the compliant device 1000 is not static, insertion of the compliant device 1000 can be done using a minimally invasive total lumbar disc replacement rather than a fusion. In some embodiments, at least one of the compliant device 1000 can be inserted alone. In alternative embodiments, the at least one of the compliant device 1000 can be implanted in tandem with any outer cage since the compliant device 1000 can be size-constrained by surgical window size. In various embodiments, the outer cage can be any cage that can be implanted into the intervertebral space and expand both laterally and vertically. In some embodiments, the outer cage is an expanding outer cage. In various embodiments the expanding outer cage can be a triaxial expanding interbody device. In alternative embodiments, the outer cage is the outer piece of a posterior inter body fusion system, such as the Flare Hawk spinal fusion device by Integrity Implants.

In various embodiments, at least one of the compliant device 1000 may be inserted with an outer expandable cage which can provide the benefit of added expandability and the disc replacement can potentially be revised to a fusion procedure with minimal hardware removal. In some embodiments, this can be achieved if the outer expanding piece is fixed to the vertebrae, while the inner actuating piece is made to be removable and can be replaced with a static insert (e.g., revision to a fusion), or with a replacement spinal disc device with equal or different mechanical properties (e.g., an identical device).

In various embodiments, the compliant devices 100, 200, 500, 600, 900 and 1000, as described herein can be manufactured using any methods. In some embodiments, the compliant devices 100, 200, 500, 600, 900 and 1000 can be designed to be any interbody device. In some embodiments, the compliant devices 100, 200, 500, 600, 900 and 1000 can be manufactured using additive manufacturing. In a particular embodiment, the additive manufacturing can be 3D printing. In some embodiments, the compliant devices 100, 200, 500, 600, 900 and 1000 can be manufactured as a single piece using additive manufacturing. In additional embodiments, the devices 100, 200, 500, 600, 900 and 1000 can be designed in a patient specific manner.

In various embodiments, the compliant devices 100, 200, 500, 600, 900 and 1000 can be manufactured from any suitable material. In some embodiments, the compliant devices 100, 200, 500, 600, 900 and 1000 can be manufactured from at least a metal including but not limited to titanium, alloy, titanium alloys, copper, aluminum, cobalt, zirconium, magnesium, chromium, stainless steel, steel, tantalum, mixtures thereof, or any other suitable metal or combinations of metals.

In some embodiments, the compliant devices 100, 200, 500, 600, 900 and 1000 can be manufactured from at least a polymer including but not limited to polyethylene (PE), polypropylene, poly methyl methacrylate (PMMA), polyetheretherketone (PEEK), polysulfone, carbon fiber, glass fiber, polytetrafluoroethylene (PTFE), high density polyethylene (HDPE), ultra-high molecular weight polyethylene, silicone rubbers, teflon, polyacetal, polyacetal polyethylene, combinations thereof, or any other suitable polymer or combination of polymers.

In some embodiments, the compliant devices 100, 200, 500, 600, 900 and 1000 can be manufactured as at least a portion of a device. In other embodiments, the compliant 100, 200, 500, 600, 900 and 1000 can be manufactured as a device. In various embodiments, the compliant devices 100, 200, 500, 600, 900 and 1000 can be manufactured as a medical device including a device for total lumbar spinal disc replacement.

In alternative embodiments, the devices 100, 200, 500, 600, 900 and 1000 can be manufactured as at least a portion of a device wherein the device is an industrial device, satellite device, medical device.

CONCLUSION

The foregoing description of the exemplary embodiments has been presented only for the purposes of illustration and description is not intended to be exhaustive or to limit the devices, systems, methods, and apparatuses herein to the precise forms disclosed. Many modifications and variations are possible considering the above teachings.

The embodiments were chosen and described in order to explain the principles of the technology discussed herein and their practical application to enable others skilled in the art to utilize the various embodiments and with various modifications as are suited to the particular use contemplated. Alternative embodiments will become apparent to those skilled in the art to which the present technologies pertain without departing from their spirit and scope.

What is claimed is:

1. A spinal disc replacement implant comprising:
a contact-aided compliant mechanism comprising:
a first rigid component;
a second rigid component;
a third rigid component;
a first flexible component;
a second flexible component;
each of the first and second flexible components comprising a first end, a second end, and a third end;
the first flexible component disposed between the first rigid component and the second rigid component;
the second flexible component disposed between the second rigid component and the third rigid component;
the first rigid component further comprising a first bearing surface, wherein the first bearing surface selectively engages an upper bearing surface of the second rigid component; and
the third rigid component further comprising a third bearing surface, wherein the third bearing surface selectively engages a lower bearing surface of the second rigid component.

2. The spinal disc replacement implant of claim 1, wherein the first and second flexible components comprise a substantially V-shape.

3. The spinal disc replacement implant of claim 2, wherein the first flexible component is disposed perpendicular to the second flexible component.

4. The spinal disc replacement implant of claim 1, wherein the first rigid component is positioned parallel to the second rigid component.

5. The spinal disc replacement implant of claim 1, wherein the first rigid component is movable in at least one degree of freedom with respect to the second rigid component.

6. The contact-aided compliant mechanism of claim 1, wherein the first bearing surface extends from one side of the first rigid component toward the second rigid component.

7. The spinal disc replacement implant of claim 6, wherein the upper bearing surface extends from one side of the second rigid component toward the first rigid component.

8. The spinal disc replacement implant of claim 6, wherein the lower bearing surface extends from one side of the second rigid component toward the third rigid component.

9. The spinal disc replacement implant of claim 1, wherein the third bearing surface extends from one side of the third rigid component toward the second rigid component.

10. The spinal disc replacement implant of claim 1, further including at least one keel.

11. The spinal disc replacement implant of claim 1, wherein at least one of the first, upper, lower, and third bearing surfaces comprises a rounded surface.

12. The contact-aided compliant mechanism of claim 1, wherein the first rigid component, second rigid component, third rigid component, first flexible component, and second flexible component are manufactured as a single part using 3D printing.

13. The spinal disc replacement implant of claim 1, wherein the first flexible component comprises a Euler spiral.

14. The spinal disc replacement implant of claim 1, wherein the second flexible component comprises a Euler spiral.

15. The spinal disc replacement implant of claim 1, wherein the first flexible component has a first stiffness and the second flexible component has a second stiffness.

16. A spinal disc replacement implant comprising:
a contact-aided compliant mechanism comprising:
a first rigid component, the first rigid component including a first bearing surface;
a second rigid component, the second rigid component including an upper and lower bearing surface;
a third rigid component, the third rigid component including a third bearing surface;
a plurality of flexible components, each of the flexible components including a first end, a second end, and a third end, wherein the first end is attached to one of the first, second, or third rigid component and wherein the third end is attached to one of the first, second, or third rigid component;
the first bearing surface selectively engaging the upper bearing surface; and
the third bearing surface selectively engaging the lower bearing surface.

17. The spinal disc replacement implant of claim 16, wherein at least one of the first, upper, lower, or third bearing surfaces has a rounded contour.

18. The spinal disc replacement implant of claim 16, wherein each of the flexible components further includes a first region disposed between the first end and the second end and a second region disposed between the second end and the third end.

19. The contact-aided compliant mechanism of claim 18, wherein the first region includes a first radius of curvature.

20. The contact-aided compliant mechanism of claim 18, wherein the second region includes a second radius of curvature.

* * * * *